US012465359B2

(12) United States Patent
Fiebig et al.

(10) Patent No.: US 12,465,359 B2
(45) Date of Patent: Nov. 11, 2025

(54) CONTROL SURFACES ON A STAPLE DRIVER OF A SURGICAL STAPLE CARTRIDGE

(71) Applicant: Cilag GmbH International, Zug (CH)

(72) Inventors: Kevin M. Fiebig, Cincinnati, OH (US); Nicholas Fanelli, Morrow, OH (US); Jeffery D. Bruns, Cincinnati, OH (US); Frederick E. Shelton, IV, Hillsboro, OH (US); Adam D. Hensel, Gahanna, OH (US); Seth D. Holdmeyer, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,793

(22) Filed: Oct. 13, 2023

(65) Prior Publication Data

US 2025/0120712 A1 Apr. 17, 2025

(51) Int. Cl.
*A61B 17/072* (2006.01)

(52) U.S. Cl.
CPC .................. *A61B 17/07207* (2013.01); *A61B 2017/07271* (2013.01)

(58) Field of Classification Search
None
See application file for complete search history.

(56) References Cited

U.S. PATENT DOCUMENTS

| | | | |
|---|---|---|---|
| 5,403,312 | A | 4/1995 | Yates et al. |
| 5,485,947 | A | 1/1996 | Olson et al. |
| 6,978,921 | B2 | 12/2005 | Shelton, IV et al. |
| 7,000,818 | B2 | 2/2006 | Shelton, IV et al. |
| 7,401,721 | B2 | 7/2008 | Holsten et al. |
| 7,407,075 | B2 | 8/2008 | Holsten et al. |
| 7,422,139 | B2 | 9/2008 | Shelton, IV et al. |
| 7,464,849 | B2 | 12/2008 | Shelton, IV et al. |
| 7,669,746 | B2 | 3/2010 | Shelton, IV |
| 7,670,334 | B2 | 3/2010 | Hueil et al. |
| 7,735,703 | B2 | 6/2010 | Morgan et al. |
| 7,753,245 | B2 | 7/2010 | Boudreaux et al. |
| 7,845,537 | B2 | 12/2010 | Shelton, IV et al. |
| 7,980,443 | B2 | 7/2011 | Scheib et al. |
| 8,123,100 | B2 | 2/2012 | Holsten et al. |
| 8,141,762 | B2 | 3/2012 | Bedi et al. |
| 8,210,411 | B2 | 7/2012 | Yates et al. |
| 8,220,688 | B2 | 7/2012 | Laurent et al. |

(Continued)

FOREIGN PATENT DOCUMENTS

| | | | |
|---|---|---|---|
| CN | 105919642 | A | 9/2016 |
| CN | 105997172 | A | 10/2016 |

(Continued)

OTHER PUBLICATIONS

U.S. Appl. No. 12/031,573, filed Feb. 14, 2008.

(Continued)

*Primary Examiner* — Tanzim Imam

(57) ABSTRACT

A surgical instrument comprising a staple cartridge including a cartridge body, staples removably stored in the cartridge body, and staple drivers movable within the cartridge body to eject, or deploy, the staples from the cartridge body is disclosed herein. The staple drivers and the cartridge body comprise control surfaces that promote the efficient deployment of the staples from the cartridge body.

14 Claims, 12 Drawing Sheets

(56) References Cited

U.S. PATENT DOCUMENTS

| | | | |
|---|---|---|---|
| 8,308,040 B2 | 11/2012 | Huang et al. | |
| 8,393,514 B2 | 3/2013 | Shelton, IV et al. | |
| 8,499,992 B2 | 8/2013 | Whitman et al. | |
| 8,540,133 B2 | 9/2013 | Bedi et al. | |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 8,864,007 B2 | 10/2014 | Widenhouse et al. | |
| 8,876,857 B2 | 11/2014 | Burbank | |
| 9,050,083 B2 | 6/2015 | Yates et al. | |
| 9,072,535 B2 | 7/2015 | Shelton, IV et al. | |
| 9,101,358 B2 | 8/2015 | Kerr et al. | |
| 9,131,940 B2 | 9/2015 | Huitema et al. | |
| 9,131,960 B2 | 9/2015 | Racz | |
| 9,345,481 B2 | 5/2016 | Hall et al. | |
| 9,386,988 B2 | 7/2016 | Baxter, III et al. | |
| 9,629,629 B2 | 4/2017 | Leimbach et al. | |
| 9,629,631 B2 | 4/2017 | Nicholas et al. | |
| 9,757,130 B2 | 9/2017 | Shelton, IV | |
| 9,770,245 B2 | 9/2017 | Swayze et al. | |
| 9,788,835 B2 | 10/2017 | Morgan et al. | |
| 9,839,420 B2 | 12/2017 | Shelton, IV et al. | |
| 9,844,369 B2 | 12/2017 | Huitema et al. | |
| 9,924,944 B2 | 3/2018 | Shelton, IV et al. | |
| 9,987,008 B2 | 6/2018 | Scirica et al. | |
| 10,080,552 B2 | 9/2018 | Nicholas et al. | |
| 10,085,749 B2 | 10/2018 | Cappola et al. | |
| 10,105,142 B2 | 10/2018 | Baxter, III et al. | |
| 10,123,798 B2 | 11/2018 | Baxter, III et al. | |
| 10,130,363 B2 | 11/2018 | Huitema et al. | |
| 10,166,023 B2 | 1/2019 | Vendely et al. | |
| 10,213,203 B2 | 2/2019 | Swayze et al. | |
| 10,299,792 B2 | 5/2019 | Huitema et al. | |
| 10,349,939 B2 | 7/2019 | Shelton, IV et al. | |
| 10,357,252 B2 | 7/2019 | Harris et al. | |
| 10,517,593 B2 | 12/2019 | Gupta et al. | |
| 10,537,324 B2 | 1/2020 | Shelton, IV et al. | |
| 10,542,981 B2 | 1/2020 | Miller et al. | |
| 10,561,419 B2 | 2/2020 | Beardsley | |
| 10,568,624 B2 | 2/2020 | Shelton, IV et al. | |
| 10,588,623 B2 | 3/2020 | Schmid et al. | |
| 10,765,427 B2 | 9/2020 | Shelton, IV et al. | |
| 10,898,183 B2 | 1/2021 | Shelton, IV et al. | |
| 10,898,191 B2 | 1/2021 | Huitema et al. | |
| 10,945,727 B2 | 3/2021 | Shelton, IV et al. | |
| 10,952,724 B2 | 3/2021 | Shelton, IV et al. | |
| 11,000,278 B2 | 5/2021 | Shelton, IV et al. | |
| 11,045,191 B2 | 6/2021 | Shelton, IV et al. | |
| 11,058,426 B2 | 7/2021 | Nalagatla et al. | |
| D933,220 S | 10/2021 | Tate et al. | |
| 11,147,552 B2 | 10/2021 | Burbank et al. | |
| 11,207,065 B2 | 12/2021 | Harris et al. | |
| 11,229,433 B2 | 1/2022 | Schings et al. | |
| 11,234,698 B2 | 2/2022 | Shelton, IV et al. | |
| 11,234,700 B2 | 2/2022 | Ragosta et al. | |
| 11,291,445 B2 | 4/2022 | Shelton, IV et al. | |
| 11,298,129 B2 | 4/2022 | Bakos et al. | |
| 11,337,693 B2 | 5/2022 | Hess et al. | |
| 11,364,029 B2 | 6/2022 | Burbank et al. | |
| 11,382,627 B2 | 7/2022 | Huitema et al. | |
| D967,421 S | 10/2022 | Shelton, IV et al. | |
| 11,490,890 B2 | 11/2022 | Harris et al. | |
| 11,517,315 B2 | 12/2022 | Huitema et al. | |
| D974,560 S | 1/2023 | Shelton, IV et al. | |
| 11,540,826 B2 | 1/2023 | Nalagatla et al. | |
| 11,571,213 B2 | 2/2023 | Huitema et al. | |
| 11,589,865 B2 | 2/2023 | Shelton, IV et al. | |
| 11,701,114 B2 | 7/2023 | Shelton, IV et al. | |
| 11,737,752 B2 | 8/2023 | Schings et al. | |
| 11,766,257 B2 | 9/2023 | Shelton, IV et al. | |
| 11,826,047 B2 | 11/2023 | Huang et al. | |
| 11,849,944 B2 | 12/2023 | Shelton, IV et al. | |
| 12,239,317 B2 | 3/2025 | Estera et al. | |
| 2007/0175955 A1 | 8/2007 | Shelton et al. | |
| 2008/0023522 A1* | 1/2008 | Olson .................. | A61B 17/105 227/175.1 |
| 2014/0001231 A1 | 1/2014 | Shelton, IV et al. | |
| 2014/0263552 A1 | 9/2014 | Hall et al. | |
| 2015/0134077 A1 | 5/2015 | Shelton, IV et al. | |
| 2018/0132849 A1 | 5/2018 | Miller et al. | |
| 2018/0168615 A1 | 6/2018 | Shelton, IV et al. | |
| 2019/0105047 A1 | 4/2019 | Nalagatla et al. | |
| 2020/0029966 A1* | 1/2020 | Zhan ................ | A61B 17/07207 |
| 2021/0121177 A1* | 4/2021 | Jasemian ......... | A61B 17/07207 |
| 2021/0298752 A1 | 9/2021 | Olson et al. | |
| 2022/0031320 A1 | 2/2022 | Hall et al. | |
| 2022/0031351 A1 | 2/2022 | Moubarak et al. | |
| 2022/0047265 A1 | 2/2022 | Miller et al. | |
| 2022/0304679 A1 | 9/2022 | Bakos et al. | |
| 2022/0346858 A1 | 11/2022 | Aronhalt et al. | |
| 2023/0119119 A1 | 4/2023 | Moubarak | |

FOREIGN PATENT DOCUMENTS

| | | |
|---|---|---|
| CN | 105997173 A | 10/2016 |
| CN | 106036848 A | 10/2016 |
| CN | 108542454 A | 9/2018 |
| CN | 111195142 A | 5/2020 |
| WO | WO-2023187646 A1 | 10/2023 |

OTHER PUBLICATIONS

U.S. Food and Drug Administration 510(k) Premarket Notification, https://www.accessdata.fda.gov/scripts/cdrh/cfdocs/cfpmn/pmn.cfm?ID=K182476, last update: Jan. 8, 2024, 1 page.

* cited by examiner

CONTROL SURFACES ON A STAPLE DRIVER OF A SURGICAL STAPLE CARTRIDGE

BACKGROUND

In various instances, a surgical stapling instrument is inserted to a patient during a surgical procedure and clamped onto patient tissue. The surgical stapling instrument can include one or more jaws that are controllable by the surgical stapling instrument. One of the jaws can comprise a staple cartridge including staples removably stored therein. Once the surgical stapling instrument is clamped onto patient tissue, the staples can be fired from the staple cartridge during a staple firing stroke.

SUMMARY

A surgical stapling instrument comprises a staple cartridge including a cartridge body, staple drivers, staples, and a sled movable from a proximal unfired position to a distal fired position during a staple firing stroke. The cartridge body comprises staple cavities defined therein and the staples are removably stored in the staple cavities. The staple drivers are translatable within the staple cavities by the sled to eject, or fire, the staples from the staple cavities during the staple firing stroke. The surgical stapling instrument further comprises an anvil that is configured to deform the staples as the staples are ejected from the staple cavities. The force needed to fire the staples during the staple firing stroke can be high, especially when the staple drivers unintentionally rotate within the staple cavities. Disclosed herein are embodiments that may reduce the force needed to perform the staple firing stroke.

LISTING OF THE FIGURES

Various features of the embodiments described herein, together with advantages thereof, may be understood in accordance with the following description taken in conjunction with the accompanying drawings as follows.

Corresponding reference characters indicate corresponding parts throughout the several views.

DETAILED DESCRIPTION

Figure 1:
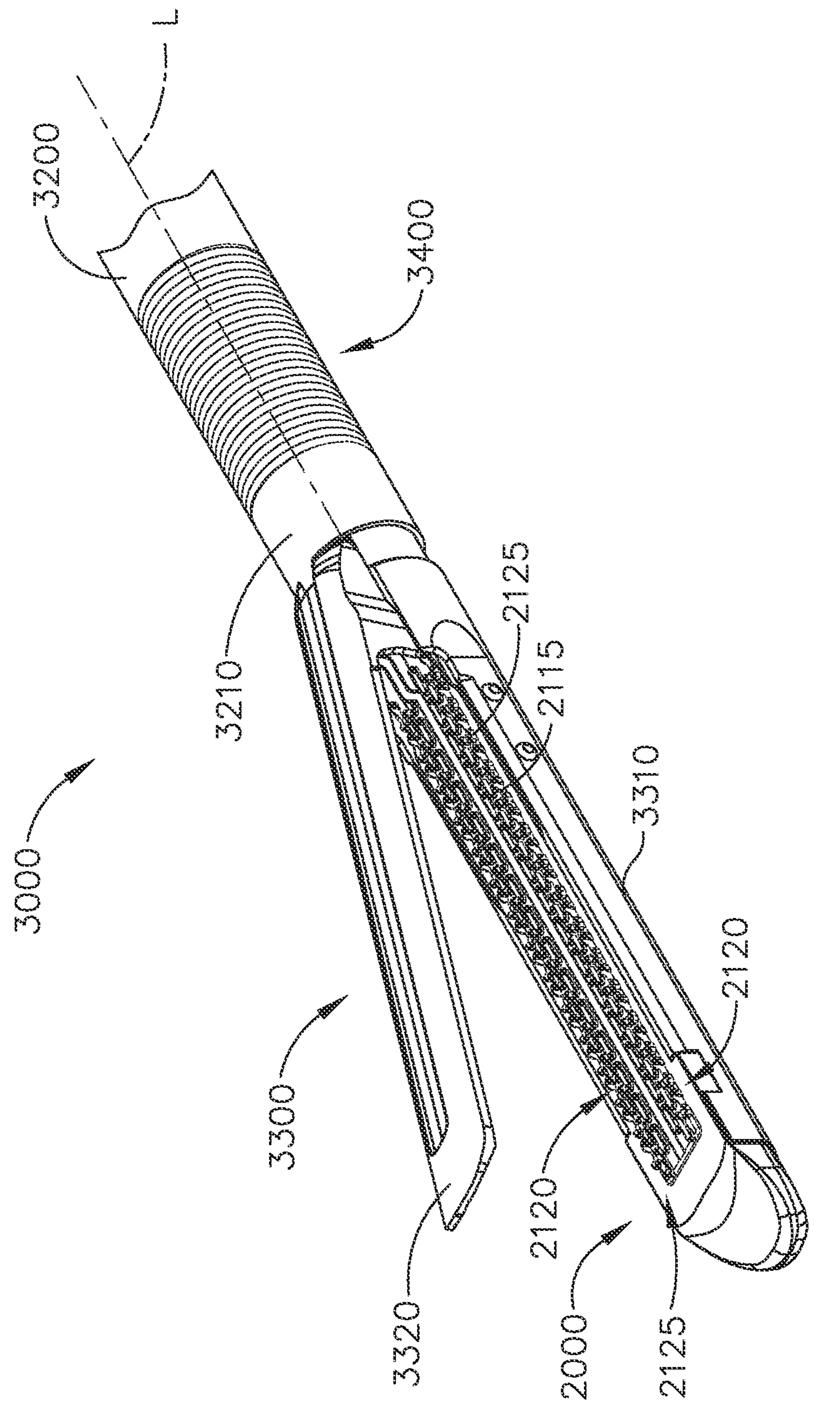
FIG. 1 is a perspective view of a distal end of a stapling instrument comprising an end effector in accordance with the present disclosure.

Applicant of the present application owns the following U.S. Patent Applications that were filed on Oct. 13, 2023 and which are each herein incorporated by reference in their respective entireties:

- U.S. patent application Ser. No. 18/379,759, titled METHOD OF OPERATING A SURGICAL STAPLING INSTRUMENT;
- U.S. patent application Ser. No. 18/379,762, titled SURGICAL STAPLING SYSTEMS WITH ADAPTIVE STAPLE FIRING ALGORITHMS;
- U.S. patent application Ser. No. 18/379,763, titled LEARNED TRIGGERS FOR ADAPTIVE CONTROL OF SURGICAL STAPLING SYSTEMS;
- U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;
- U.S. patent application Ser. No. 18/379,768, titled PROPORTIONATE BALANCING OF THE FUNCTION IMPACT MAGNITUDE OF BATTERY OUTPUT TO PEAK MOTOR CURRENT;
- U.S. patent application Ser. No. 18/379,771, titled MOTOR OPTIMIZATION BY MINIMIZATION OF PARASITIC LOSSES AND TUNING MOTOR DRIVE CONFIGURATION;
- U.S. patent application Ser. No. 18/379,773, titled APPARATUS AND METHOD TO REDUCE PARASITIC LOSSES OF THE ELECTRICAL SYSTEM OF A SURGICAL INSTRUMENT;
- U.S. patent application Ser. No. 18/379,776, titled SURGICAL TOOL WITH RELAXED FLEX CIRCUIT ARTICULATION;
- U.S. patent application Ser. No. 18/379,777, titled WIRING HARNESS FOR SMART STAPLER WITH MULTI AXIS ARTICULATION;
- U.S. patent application Ser. No. 18/379,781, titled SURGICAL SYSTEM WITH WIRELESS ARRAY FOR POWER AND DATA TRANSFER;
- U.S. patent application Ser. No. 18/379,784, titled SURGICAL STAPLE CARTRIDGE COMPRISING REPLACEABLE ELECTRONICS PACKAGE.

Applicant of the present application owns the following U.S. Patent Applications that were filed on Oct. 13, 2023 and which are each herein incorporated by reference in their respective entireties:

- U.S. patent application Ser. No. 18/379,790, titled METHOD OF ASSEMBLING A STAPLE CARTRIDGE;
- U.S. patent application Ser. No. 18/379,796, titled INTEGRAL CARTRIDGE STIFFENING FEATURES TO REDUCE CARTRIDGE DEFLECTION;
- U.S. patent application Ser. No. 18/379,801, titled STAPLE CARTRIDGE COMPRISING WALL STRUCTURES TO REDUCE CARTRIDGE DEFLECTION;
- U.S. patent application Ser. No. 18/379,803, titled PANLESS STAPLE CARTRIDGE ASSEMBLY COMPRISING RETENTION FEATURES FOR HOLDING STAPLE DRIVERS AND SLED;
- U.S. patent application Ser. No. 18/379,805, titled STAPLE CARTRIDGE COMPRISING A SLED HAVING A DRIVER LIFT CAM;
- U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;
- U.S. patent application Ser. No. 18/379,810, titled STAPLE CARTRIDGE COMPRISING A COMPOSITE SLED;
- U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;
- U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;
- U.S. patent application Ser. No. 18/379,817, titled DUAL INDEPENDENT KEYED LOCKING MEMBERS ACTING ON THE SAME DRIVE MEMBER;
- U.S. patent application Ser. No. 18/379,820, titled ADJUNCTS FOR USE WITH SURGICAL STAPLING INSTRUMENTS;
- U.S. patent application Ser. No. 18/379,822, titled ADJUNCTS FOR USE WITH SURGICAL STAPLING INSTRUMENTS;
- U.S. patent application Ser. No. 18/379,826, titled JAW CONTROL SURFACES ON A SURGICAL INSTRUMENT JAW;
- U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;
- U.S. patent application Ser. No. 18/379,831, titled STAPLE CARTRIDGES COMPRISING TRACE RETENTION FEATURES;
- U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing driver. The firing driver is configured to contact the sled and push the sled toward the distal end. The longitudinal slot defined in the cartridge body is configured to receive the firing driver. The anvil also includes a slot configured to receive the firing driver. The firing driver further comprises a first cam which engages the first jaw and a second cam which engages the second jaw. As the firing driver is advanced distally, the first cam and the second cam can control the distance, or tissue gap, between the deck of the staple cartridge and the anvil. The firing driver also comprises a knife configured to incise the tissue captured intermediate the staple cartridge and the anvil. It is desirable for the knife to be positioned at least partially proximal to the ramped surfaces such that the staples are ejected ahead of the knife.

A surgical stapling instrument 3000 is illustrated in FIG. 1. The stapling instrument 3000 comprises a handle, an elongate shaft 3200 extending from the handle, and an end effector 3300 including a cartridge jaw 3310 and an anvil jaw 3320. The handle comprises triggers that are actuatable by a clinician to operate the stapling instrument 3000 as described further below. The stapling instrument 3000 may comprise a housing assembly configured to be attached to a robotic surgical instrument system instead of the handle. The housing assembly may comprise rotatable inputs that are operably coupled with motor-driven outputs of the robotic surgical instrument system when the housing assembly is attached to the robotic surgical instrument system. The robotic surgical instrument system comprises a control station including triggers that are actuatable by a clinician to operate the surgical instrument 3000. The entire disclosure of U.S. Pat. No. 9,072,535, entitled SURGICAL STAPLING INSTRUMENT WITH ROTATABLE DEPLOYABLE ARRANGEMENTS, which issued on Jul. 7, 2015, is incorporated by reference herein.

The elongate shaft 3200 is rotatable relative to handle about a longitudinal axis L. When the elongate shaft 3200 is rotated relative to the handle, the end effector 3300 rotates with the elongate shaft 3200. The handle comprises a rotation actuator mounted to the elongate shaft 3200 that is rotatable relative to the handle by the clinician to rotate the shaft 3200 about the longitudinal axis L. In accordance with the present disclosure, the stapling instrument 3000 may comprise a motor-driven system that is operable to rotate the elongate shaft 3200. Further, in accordance with the present disclosure, the motor-driven system may comprise an electric motor mounted in the handle that may include an output gear meshingly engaged with a ring of gear teeth defined on the elongate shaft 3200. The motor-driven system further comprises a trigger, such as a switch, for example, accessible by the clinician operating the stapling instrument 3000.

The end effector 3300 is rotatable relative to the shaft 3200 about an articulation joint 3400. The articulation joint 3400 defines an articulation axis about which the end effector 3300 is articulated relative to the shaft 3200. The articulation joint 3400 also defines a plane within which the end effector 3300 is articulated relative to the shaft 3200. The stapling instrument 3000 further comprises an articulation drive system including an articulation driver engaged with the end effector 3300, an electric motor operable to drive the articulation driver longitudinally, and a motor control circuit including a trigger, such as a switch, for example, accessible by the clinician operating the stapling instrument 3000. When the articulation driver is translated distally by the articulation drive system, the end effector 3300 rotates in a first direction and, when the articulation driver is translated proximally by the articulation drive system, the end effector 3300 rotates in a second, or opposite, direction. In accordance with the present disclosure, the articulation joint 3400 can define more than one articulation axis, such as two articulation axes, for example, about which the end effector 3300 can be rotated relative to the shaft 3200. In accordance with the present disclosure, the articulation joint 3400 may comprise a flexible articulation region. The entire disclosure of U.S. Pat. No. 9,629,629, entitled CONTROL SYSTEMS FOR SURGICAL INSTRUMENTS, which issued on Apr. 25, 2017, is incorporated by reference herein.

Figure 2:
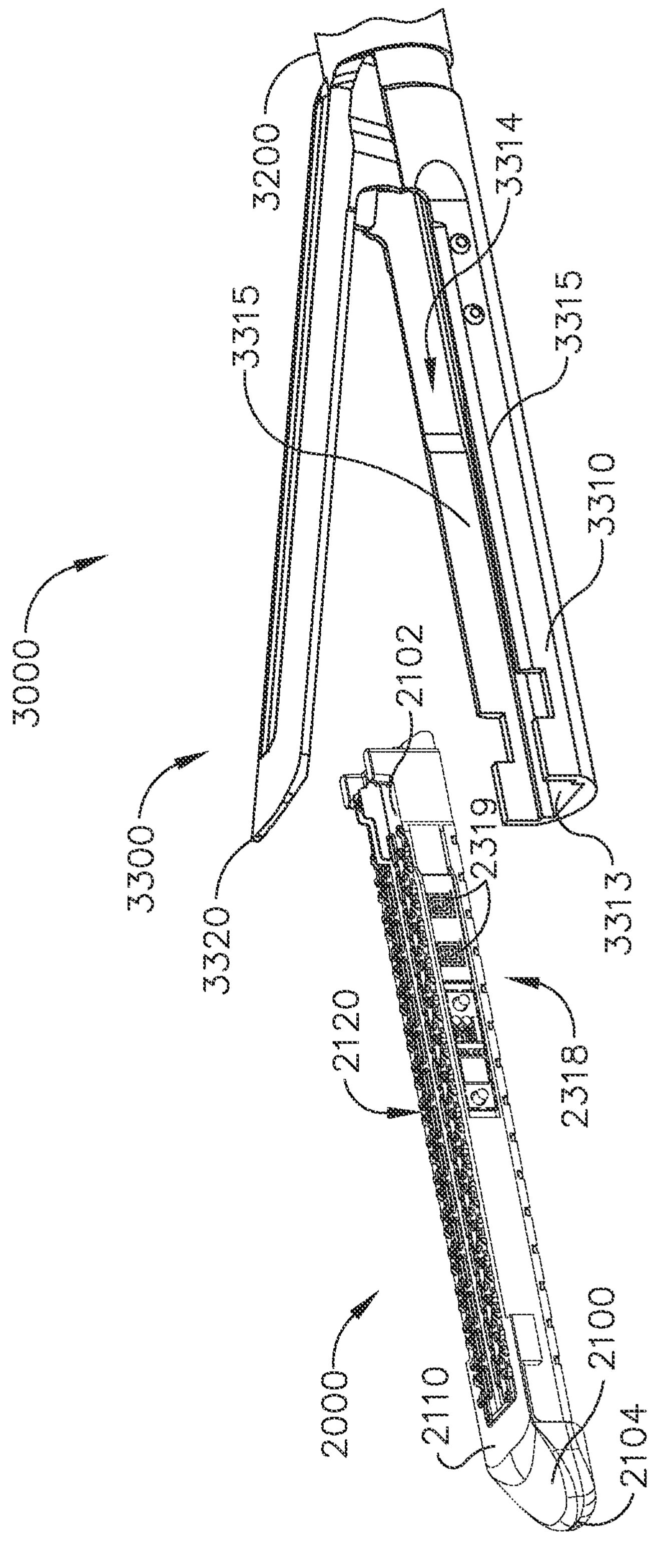
FIG. 2 is a perspective view of the end effector of FIG. 1 illustrating a replaceable staple cartridge removed from a cartridge jaw of the end effector.
Figure 3:
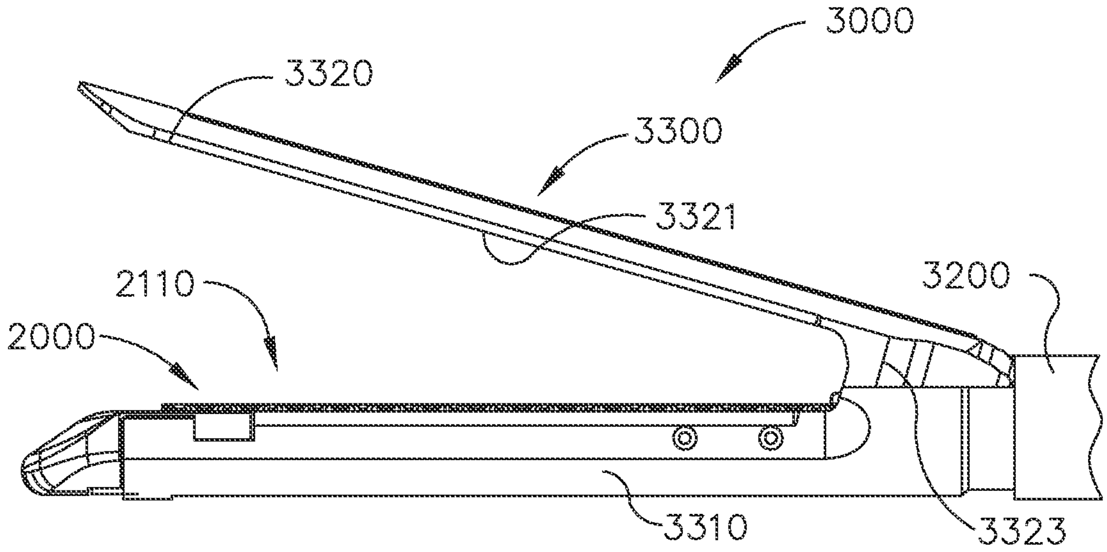
FIG. 3 is an elevational view of the end effector of FIG. 1 illustrating an anvil jaw of the end effector in an open position.
Figure 4:
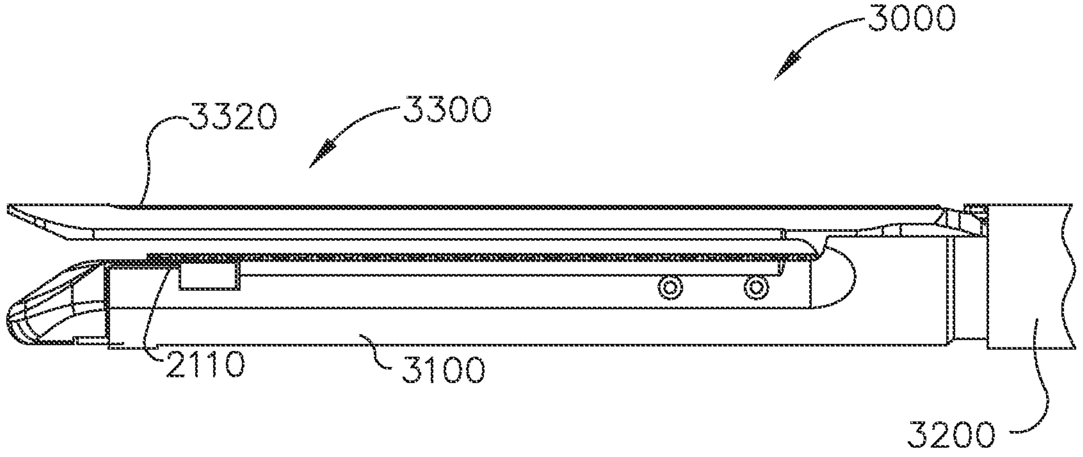
FIG. 4 is an elevational view of the end effector of FIG. 1 illustrating the anvil jaw of FIG. 3 in a closed position.

Referring to FIG. 2, the cartridge jaw 3310 of the end effector 3300 comprises a channel 3314 configured to receive a replaceable staple cartridge 2000, for example. The channel 3314 comprises a bottom 3313 and lateral sidewalls 3315 extending upwardly from the bottom 3313. The staple cartridge 2000 comprises a cartridge body 2100 including a proximal end 2102, a distal end 2104, a deck 2110 configured to support patient tissue thereon, and longitudinal rows of staple cavities 2120 defined in the deck 2110. Referring to FIGS. 3 and 4, the anvil jaw 3320 of the end effector 3300 is rotatably connected to the cartridge jaw 3310 such that the anvil jaw 3320 is rotatable about a pivot axis. The anvil jaw 3320 comprises a tissue compression surface 3321 that is brought into opposition with the deck 2110 of the staple cartridge 2000 when the anvil jaw 3320 is rotated from a fully-open position (FIG. 3) into a fully-closed position (FIG. 4). The above being said, alternative embodiments are envisioned in which the cartridge jaw 3310 is movable relative to the anvil jaw 3320.

Further to the above, the anvil jaw 3320 is movable from a fully-open position (FIG. 3) to a fully-closed position (FIG. 4) to clamp tissue between the anvil jaw 3320 and the staple cartridge 2000. The stapling instrument 3000 further comprises a jaw closure system configured to move the anvil jaw 3320 into its fully-closed position. The jaw closure system comprises a trigger rotatably coupled to the handle, a closure carriage positioned in the handle translatable distally by the trigger, and a closure tube 3210 supported by the closure carriage such that the closure tube 3210 translates with the closure carriage. The trigger comprises a rotatable lever movable from an unactuated position to an actuated position to transmit a force applied to the trigger by a clinician to the closure tube 3210. When the trigger is pulled toward a grip of the handle by the clinician, the trigger pushes the closure carriage and the closure tube 3210 distally.

In accordance with the present disclosure, the jaw closure system may comprise an electric motor configured to drive the closure tube 3210 distally through the closure stroke when the electric motor is operated in a first direction and retract the closure tube 3210 proximally when the electric motor is operated in a second, or opposite, direction. Further, in accordance with the present disclosure, the jaw closure system may comprise a motor control circuit configured to control the operation of the electric motor. The motor control circuit comprises a processor and a trigger that is actuatable by the clinician to operate the electric motor. That said, any suitable motor actuation system can be utilized.

The staple cartridge 2000 and/or the cartridge jaw 3310 comprise features which releasably lock the staple cartridge 2000 in the cartridge jaw 3310 such that the staple cartridge 2000 is secured, or seated, in position in the cartridge jaw 3310 but can be replaced during a surgical procedure. The staple cartridge 2000 can be secured in the cartridge jaw 3310 in a manner that does not allow the staple cartridge 2000 to be released from the cartridge jaw 3310 and replaced during a surgical procedure. The entire disclosure of U.S. Pat. No. 11,045,191, entitled METHOD FOR OPERATING A SURGICAL STAPLING SYSTEM, which issued on Jun. 29, 2021 is incorporated by reference herein.

Figure 5:
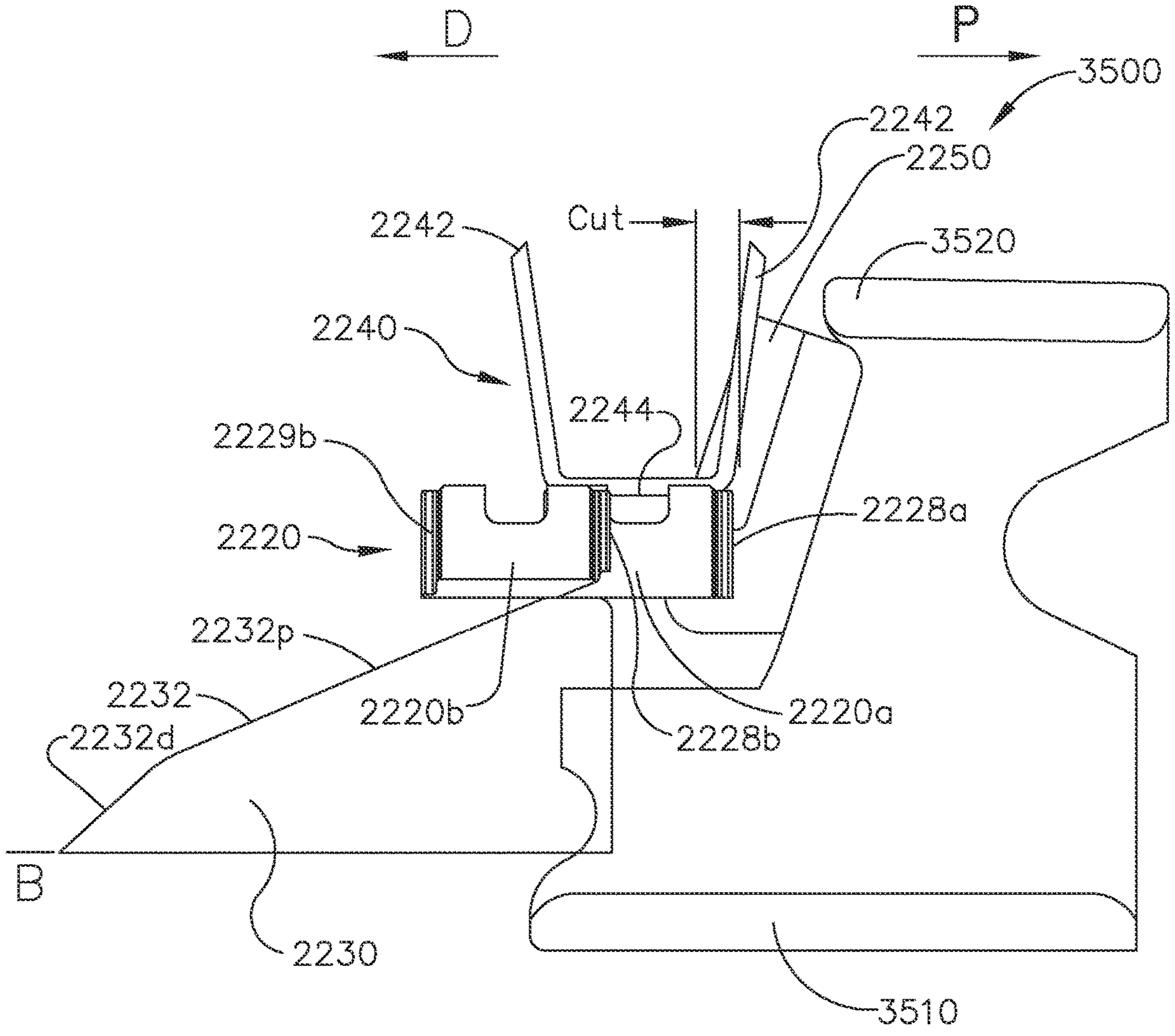
FIG. 5 is an elevational view of a firing driver of the stapling instrument of FIG. 1 and a sled, staple driver, and staple of the staple cartridge of FIG. 2.

Referring primarily to FIG. 5, the staple cartridge 2000 further comprises staples 2240 stored in the staple cavities 2120 and staple drivers 2220 movable within the staple cavities 2120 to eject the staples 2240 from the staple cavities 2120 during a staple firing stroke. As discussed further below, each staple driver 2220 is configured to support and drive, i.e., fire, three staples 2240; however, other embodiments are envisioned in which one or more staple drivers of the staple cartridge 2000 are configured to fire more than three staples or less than three staples. Referring to FIG. 5, the staple cartridge 2000 further comprises a sled 2230 movable from a proximal position to a distal position by a firing driver 3500 of the stapling instrument 3000 during the staple firing stoke to lift the staple drivers 2220 within the staple cavities 2120 and eject the staples 2240 from the staple cartridge 2000.

Further to the above, referring again to FIG. 5, the sled 2230 comprises at least one ramp 2232 configured to engage and slide under the staple drivers 2220 as the sled 2230 is moved distally during the staple firing stroke. As the ramp 2232 passes under a staple driver 2220, the ramp 2232 moves the staple driver 2220 upwardly within three staple cavities 2120 so that the staples 2240 positioned within the three staple cavities 2120 are simultaneously driven upwardly toward the anvil jaw 3320 positioned opposite the staple cartridge 2000. The staple driver 2220 can move from an unfired position at the bottom of the staple cavities 2120 to a fired position in which the staple driver 2220 is supported by the top, or apex, of the ramp 2232 as illustrated in FIG. 5. Once the staple driver 2220 has reached the fully-fired position illustrated in FIG. 5, the three staples driven by the staple driver 2220 have been deformed into their fully-fired or fully-deformed configuration. Such a fully-fired configuration of the staples 2240 may comprise a B-shaped configuration, for example, in which the legs 2242 of the staples 2240 have been bent inwardly and downwardly toward their bases 2244. Notably, the staple 2240 in FIG. 5 is depicted in its unfired configuration- and not its fired configuration. In this fully-fired position of the staple driver 2220, however, the reader should appreciate that the staple 2240 will have already been deformed into its fully-fired or deformed configuration.

Referring again to FIG. 5, the sled 2230 further comprises a tissue cutting knife 2250 incise patient tissue during the staple firing stroke. The tissue cutting knife 2250 comprises a distally-presented knife edge that moves within a longitudinal slot 2115 defined in the cartridge body 2100. Prior to the staple firing stroke, the sled 2230 is positioned in an unfired position at the proximal end 2102 of the staple cartridge 2000. In this position, the tissue cutting knife 2250 extends above the deck 2110 of the cartridge body 2100 between two knife guards extending upwardly from the deck. As the sled 2230 is advanced distally toward the distal end 2104 of the staple cartridge 2000 during the staple firing stroke, the tissue cutting knife 2250 is exposed and can cut the patient tissue captured between the staple cartridge 2000 and the anvil jaw 3320. In accordance with the present disclosure, the sled of the staple cartridge 2000 may not include a tissue cutting knife. Further, in accordance with the present disclosure, the firing driver 3500, for example, may comprise a tissue cutting knife.

The anvil jaw 3320 further comprises staple forming pockets arranged in longitudinal rows that are registered with the staple cavities 2120 defined in the staple cartridge 2000 when the anvil jaw 3320 is in its fully-closed position. The anvil jaw 3320 further comprises tissue stops 3323 that extend downwardly toward the cartridge jaw 3310 and are positioned inwardly with respect to the lateral sides of the cartridge jaw 3310. The tissue stops 3323 inhibit the migration of tissue proximally into the end effector 3300 past the tissue stops 3323 which can reduce the possibility of the tissue coming into contact with a tissue cutting edge of the tissue cutting knife 3250 parked in its proximal unfired position.

Referring again to FIG. 5, the firing driver 3500 comprises a first cam 3510 configured to engage the cartridge jaw 3310 during the staple firing stroke. Similarly, the firing driver 3500 comprises a second cam 3520 configured to engage the anvil jaw 3320 during the staple firing stroke. During the staple firing stroke, the first cam 3510 and the second cam 3520 position the anvil jaw 3320 relative to the staple cartridge 2000 in the cartridge jaw 3310 such that the staples 2240 ejected from the staple cartridge 2000 contact the forming pockets defined in the anvil jaw 3320 and are deformed to a suitable deformed height, or a deformed height within a suitable height range. Notably, the second cam 3520 is positioned vertically above the first cam 3510 and at least a portion of the tissue cutting knife 2250 is positioned vertically intermediate the first cam 3510 and the second cam 3520. Moreover, notably, at least a portion of the staple 2240 depicted in FIG. 5 is positioned distally with respect to the tissue cutting knife 2250. Although not depicted in FIG. 5, the staple driver 2220 is configured to support two additional staples 2240—one staple 2240 that is laterally aligned with and parallel to the depicted staple 2240 and another staple 2240 that is positioned distally with respect to the two laterally aligned staples 2240. As a result of the staples 2240 being positioned distally, or at least partially distally, with respect to the tissue cutting knife 2250, the patient tissue is stapled before it is transected by the tissue cutting knife 2250 during the staple firing stroke.

Figure 6:
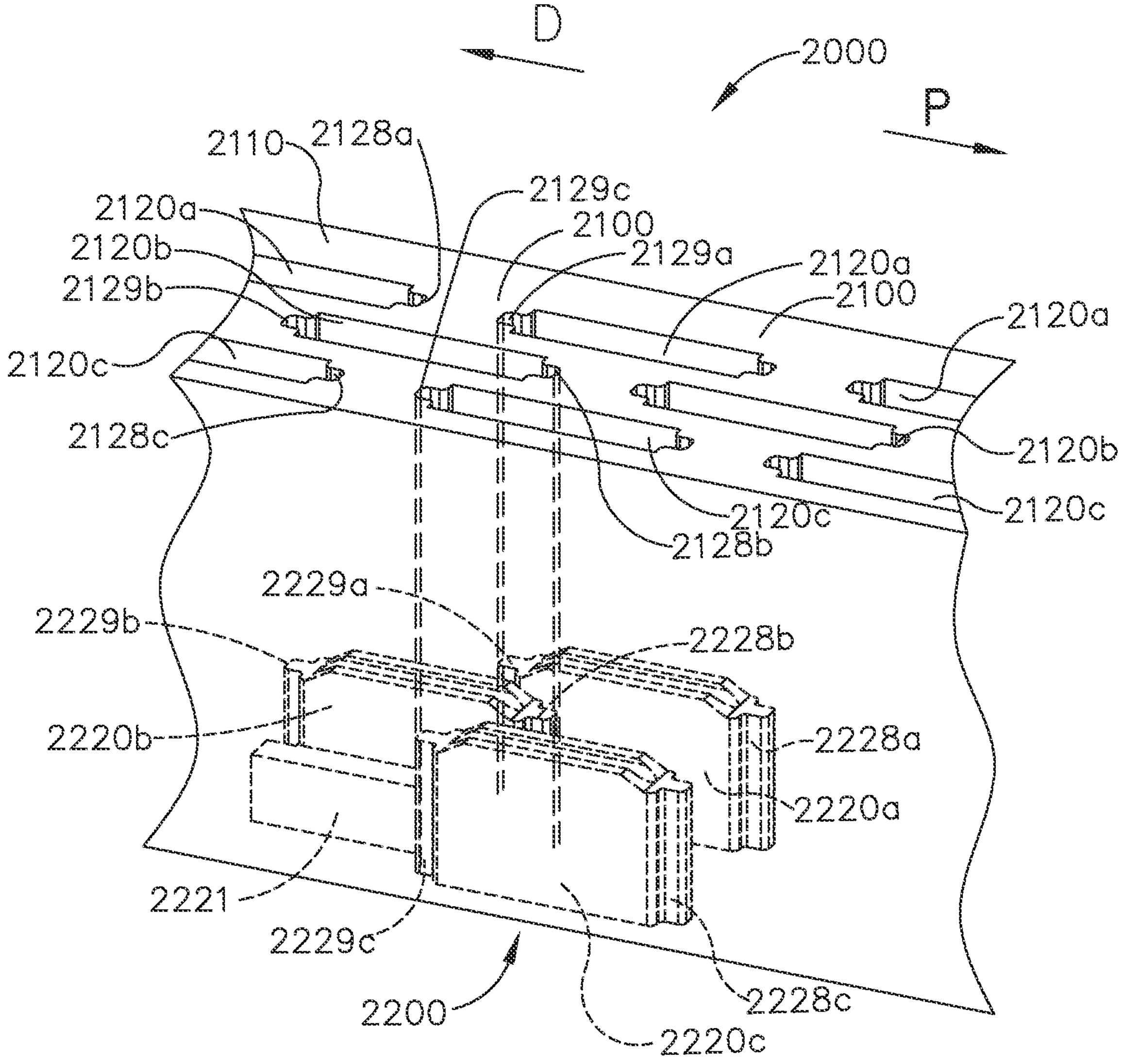
FIG. 6 is a partial perspective view of the staple cartridge of FIG. 2.
Figure 7:
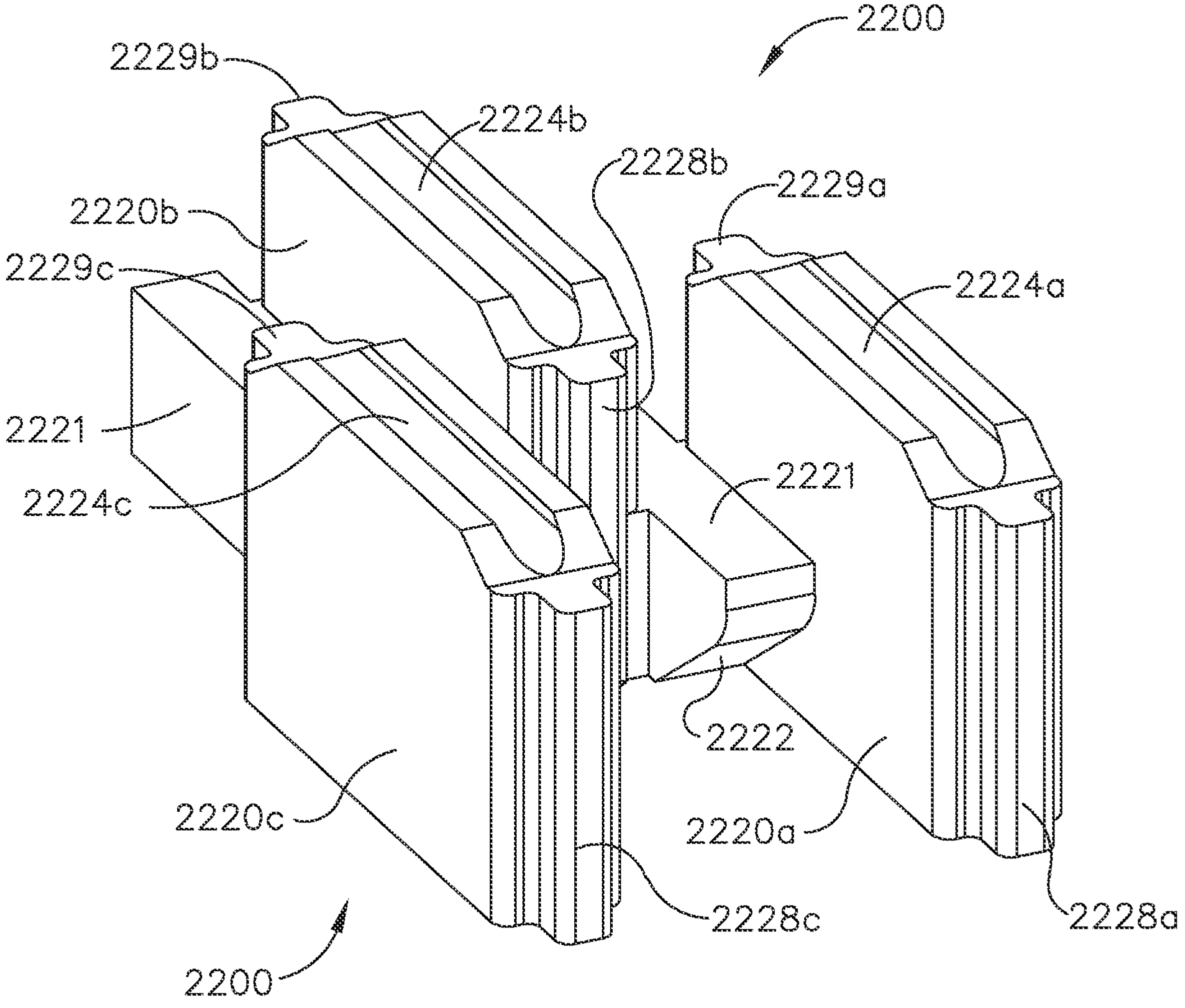
FIG. 7 is a perspective view of the staple driver of FIG. 5.

Referring again to FIG. 1, the cartridge body 2100 of the staple cartridge 2000 comprises six longitudinal rows of staple cavities 2120—three longitudinal rows on a first side of the longitudinal slot 2115 and three longitudinal rows on a second, or opposite, side of the longitudinal slot 2115. The staple drivers 2220 are arranged in two longitudinal rows—a first row on the first side of the longitudinal slot 2115 and a second row on the second side of the longitudinal slot 2115. Referring to FIGS. 6 and 7, each staple driver 2220 comprises three drive pillars—a first drive pillar **2220*a*, a second drive pillar 2220*b*, and a third drive pillar 2220*c*—arranged in an arrow-like, or echelon-like, arrangement. The first drive pillar 2220*a* is positioned within a first staple cavity 2120*a* in a first longitudinal row, the second drive pillar 2220*b* is positioned within a second staple cavity 2120*b* in a second longitudinal row, and the third drive pillar 2220*c* is positioned within a third staple cavity 2120*c* in a third longitudinal row. The first pillar 2220*a*** and the second pillar

2220*b* are connected by a connector 2221 and, similarly, the second pillar 2220*b* and the third pillar 2220*c* are connected by another connector 2221. The second pillar 2220*b* is positioned distally, at least partially, with respect to the first pillar 2220*a* and the third pillar 2220*c*. The first pillar 2220*a* is positioned laterally with respect to and aligned with the third pillar 2220*c*. Each drive pillar comprises a seat, or cradle, that is configured to receive a base 2244 of a staple 2240 and drive the staple 2240 upwardly as the staple driver 2220 is lifted upwardly by the sled 2230. More specifically, the first drive pillar 2220*a* comprises a first cradle 2224*a* configured to receive and drive the base 2244 of a first staple 2240, the second drive pillar 2220*b* comprises a second cradle 2224*b* configured to receive and drive the base 2244 of a second staple 2240, and the third drive pillar 2220*c* comprises a third cradle 2224*c* configured to receive and drive the base of a third staple 2240.

In each longitudinal row of staple drivers 2220, the staple drivers 2220 are arranged in a nested manner wherein the first drive pillars 2220*a*, and the first cradles 2224*a* defined thereon, are longitudinally aligned with one another such that the staples supported by and driven by the first drive pillars 2220*a* during the staple firing stroke form a first longitudinal line of staples in the patient tissue. Similarly, the second drive pillars 2220*b*, and the second cradles 2224*b* defined thereon, are longitudinally aligned with one another such that the staples supported by and driven by the second drive pillars 2220*b* during the staple firing stroke form a second line of staples in the patient tissue. Also, similarly, the third drive pillars 2220*c*, and the third cradles 2224*c* defined thereon, are longitudinally aligned with one another such that the staples supported by and driven by the third drive pillars 2220*c* during the staple firing stroke form a third line of staples in the patient tissue.

As described above, the sled 2230 is moved distally during the staple firing stroke to engage the staple drivers 2220 and drive the staple drivers 2220 toward the anvil jaw 3120 positioned opposite the staple cartridge 2000. At the outset of the staple firing stroke, the sled 2230 comes into contact with the proximal-most staple driver 2220 in the first longitudinal row of staple drivers 2220 and the proximal-most staple driver 2220 in the second longitudinal row of staple drivers 2220 and lifts these two proximal-most drivers 2220 toward the anvil jaw 3120. As the sled 2230 is moved further distally by the firing driver 3500 during the staple firing stroke, the sled 2230 sequentially engages the remainder of the staple drivers 2220 in the longitudinal rows of staple drivers 2220 until all of the staple drivers 2220 have been lifted to their fully-fired positions and/or the staple firing stroke is stopped early and the firing driver 3500 is retracted. As a result of the above, the staple drivers 2220 within a longitudinal row of staple drivers 2220 move relative to one another during the staple firing stroke. When the staple drivers 2220 are in their unfired positions, the second pillars 2220*b* of the staple drivers 2220 are positioned intermediate, or at least partially positioned intermediate, the first and third pillars 2220*a*, 2220*c* of the staple driver 2220 positioned distally in front of it owing to the nested arrangement of the staple drivers 2220 within a longitudinal row. As a staple driver 2220 is lifted relative to the staple driver 2220 positioned distally in front of it, the staple drivers 2220 un-nest and then re-nest when the staple drivers 2220 reach their fired positions. Each staple driver 2220 comprises two ramp, or inclined, surfaces 2222—one on each connector 2221—that are engaged by the sled 2230 during the staple firing stroke to lift the staple driver 2220 as described above.

Referring again to FIGS. 6 and 7, the first pillar 2220*a* of each staple driver 2220 comprises a proximal guide rail 2228*a* extending proximally from the proximal end of the cradle 2224*a* and a distal guide rail 2229*a* extending distally from the distal end of the cradle 2224*a*. Each proximal guide rail 2228*a* is slideably received in a proximal rail slot 2128*a* of a first staple cavity 2120*a* and, likewise, each distal guide rail 2229*a* is slideably received in a distal rail slot 2129*a*. Similarly, the second pillar 2220*b* of each staple driver 2220 comprises a proximal guide rail 2228*b* extending proximally from the proximal end of the cradle 2224*b* and a distal guide rail 2229*b* extending distally from the distal end of the cradle 2224*b*. Each proximal guide rail 2228*b* is slideably received in a proximal rail slot 2128*b* of a first staple cavity 2120*b* and, likewise, each distal guide rail 2229*b* is slideably received in a distal rail slot 2129*b*. Also, similarly, the third pillar 2220*c* of each staple driver 2220 comprises a proximal guide rail 2228*c* extending proximally from the proximal end of the cradle 2224*c* and a distal guide rail 2229*c* extending distally from the distal end of the cradle 2224*c*. Each proximal guide rail 2228*c* is slideably received in a proximal rail slot 2128*c* of a third staple cavity 2120*c* and, likewise, each distal guide rail 2229*c* is slideably received in a distal rail slot 2129*c*.

Further to the above, referring again to FIGS. 5 and 7, the ramps 2232 of the sled 2230 are configured to engage the ramp surfaces 2222 of the staple drivers 2220 and push the staple drivers 2220 upwardly within the staple cavities 2120. The sled 2230 comprises four ramps 2232—two ramps 2232 on a first side of the sled 2230 that engage the staple drivers 2220 in the first longitudinal row of staple drivers 2220 and two ramps 2232 on a second, or opposite, side of the longitudinal slot 2115 that engage the staple drivers 2220 in the second longitudinal row of staple drivers 2220. The interface between the ramps 2232 of the sled 2230 and the ramp surfaces 2222 of a staple driver 2220 creates a reaction force that pushes the staple driver 2220 upwardly within its staple cavity 2210 but also pushes the staple driver 2220 distally, or longitudinally, into contact with the distal side-walls of the staple cavity 2210. As a result of the longitudinal component of this reaction force, absent other considerations, referring again to FIGS. 6 and 7, the distal guide rail 2229*a* of the staple driver 2220 may engage the distal end wall of the distal rail slot 2129*a* of the cartridge body 2100, the distal guide rail 2229*b* of the staple driver 2220 may engage the distal end wall of the distal rail slot 2129*b* of the cartridge body 2100, and/or the distal guide rail 2229*c* of the staple driver 2220 may engage the distal end wall of the distal rail slot 2129*c* of the cartridge body 2100. Such contact between the distal guide rails 2229*a*, 2229*b*, 2229*c* and the distal end walls of the distal rail slots 2129*a*, 2129*b*, 2129*c* controls the motion of the staple driver 2220 and could, absent more, create large friction forces, and possibly binding, between the staple driver 2220 and the cartridge body 2100. The staple driver 2220 can still be lifted to fire the staples supported thereon during the staple firing stroke, but the force needed to push the sled 2230 distally to lift the staple driver, or drivers, 2220 experiencing such friction and/or binding could be high.

In accordance with the present disclosure, further to the above, the staple drivers 2220 in a longitudinal row of staple drivers 2220 can support each other longitudinally. A staple driver 2220 being lifted by the sled 2230 can be shifted into contact with the staple driver 2220 positioned distally in front of it. Alternatively, the staple drivers 2220 can be in contact with one another without having to be shifted distally by the sled 2230. Longitudinally-adjacent staple drivers 2220 can be in contact with one another in their unlifted positions. In either event, in accordance with the present disclosure, the distal rails 2229*a* of the staple drivers 2220 can be in contact with the distal ends of the distal rail slots 2129*a* and the distal rails 2229*c* of the staple drivers 2220 can be in contact with the distal ends of the distal rail slots 2129*c* as the staple drivers 2220 are lifted from their unfired position to their fired position. The distal rails 2229*b* of a staple driver 2220 being lifted by the sled 2230 can be in contact with the staple driver 2220 positioned distally in front of it. More specifically, the distal rail 2229*b* of the staple driver 2220 being lifted by the sled 2230 can be in sliding contact with the proximal rail 2228*b* of the staple driver 2220 positioned distally in front of it. In accordance with the present disclosure, the rails 2228*b* and 2229*b* of the drivers 2220 may comprise control surfaces. Further, in accordance with the present disclosure, the distal rail 2229*a* of each staple driver 2220 may slidingly engages the proximal rail 2228*a* of the staple driver 2220 positioned distally in front of it and, similarly, the distal rail 2229*c* of each staple driver 2220 may slidingly engage the proximal rail 2228*c* of the staple driver 2220 positioned in front of it. The distal rails 2229*b* of the staple drivers 2220 can be slidingly engaged with the cartridge body 2100. The rails 2228*a*, 2229*a*, 2228*c*, and 2229*c* of the drivers 2220 may comprise control surfaces.

Figure 8:
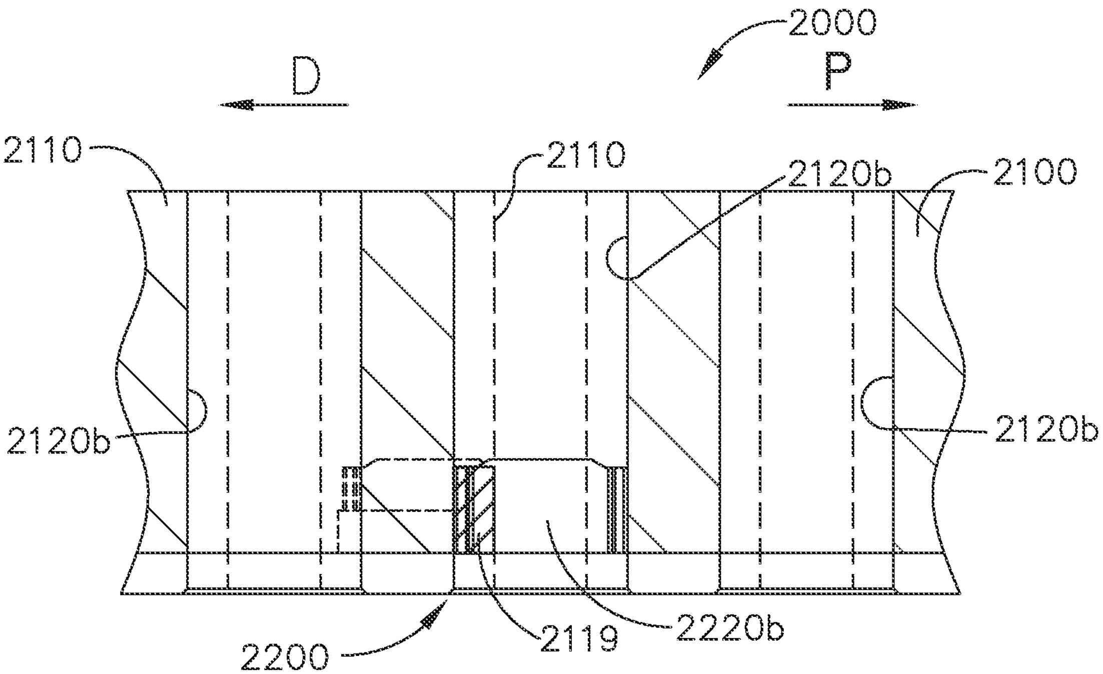
FIG. 8 is a partial cross-sectional elevational view of the staple cartridge of FIG. 2.

Further to the above, referring to FIG. 6, the interaction surfaces between the staple drivers 2220 and the sidewalls of the staple cavities 2120 can be controlled, or selected, so as to lower the force needed to lift the staple drivers 2220 within the staple cavities 2120. More specifically, in accordance with the present disclosure, the staple drivers 2220 and the staple cavities 2120 can be configured and arranged such that the distal guide rails 2229*a* of the staple drivers 2220 are in contact with the distal ends of the distal rail slots 2129*a* of the staple cavities 2120 as the staple drivers 2220 are moved from their unfired positions to their fired positions during the staple firing stroke. Similarly, the distal guide rails 2229*c* of the staple drivers 2220 can be in contact with the distal ends of the distal rail slots 2129*c* of the staple cavities 2120 as the staple drivers 2220 are moved from their unfired positions to their fired positions during the staple firing stroke. That said, the staple drivers 2220 and the staple cavities 2120 are configured and arranged such that the proximal guide rails 2228*b* of the staple drivers 2220 are in contact with the proximal ends of the proximal rail slots 2128*b* of the staple cavities 2120 as the staple drivers 2220 are moved from their unfired positions to their fired positions during the staple firing stroke. As such, the guide rails 2229*a*, 2228*b*, and 2229*c* of the staple drivers 2220 and the guide rail slots 2129*a*, 2128*b*, and 2129*c* of the staple cavities 2120 comprise control surfaces which constrain the longitudinal movement of the staple drivers 2220 as the staple drivers 2220 are engaged by the sled 2230. In accordance with the present disclosure, at least one portion of the staple drivers 2220 can be flexible so as to permit the guide rails 2229*a*, 2228*b*, and 2229*c* to be in simultaneous contact with the ends of the guide rail slots 2129*a*, 2128*b*, and 2129*c*, respectively. Referring to FIG. 8, the connectors 2221 of each staple driver 2220 can be sufficiently flexible to permit the pillars 2220*a*, 2220*b*, and 2220*c* of the staple driver 2220 to engage the cartridge body 2100 in a bearing zone 2119 (represented by a cross-hatched area). Each staple driver 2220 may be comprised of a unitary piece of material, such as plastic, for example, and the connectors 2221 comprise cut-outs defined therein which permit the connects 2221 to elastically stretch and permit the guide rails 2229*a*, 2228*b*, and 2229*c* to be in simultaneous contact with the guide rail slots 2129*a*, 2128*b*, and 2129*c*, respectively. In accordance with the present disclosure, each staple driver 2220 may be comprised of two or more materials. For instance, the pillars 2220*a*, 2220*b*, and 2220*c* of the staple driver 2220 may be comprised of a stiff plastic material, such as a glass fiber-reinforced material plastic material, for example, and the connectors 2221 may be comprised of a less stiff, or more flexible, plastic material. In accordance with the present disclosure, the more flexible material comprising the connectors 2221 may not have glass fiber-reinforcement or may have less glass-fiber reinforcement than the pillars 2220*a*, 2220*b*, and 2220*c*.

Further to the above, referring again to FIGS. 6 and 7, the proximal rails 2228*a* of the staple drivers 2220 are not in contact with the proximal ends of the proximal rail slots 2128*a* of the cartridge body 2100. Similarly, the distal rails 2229*b* of the staple drivers 2220 are not in contact with the distal ends of the distal rail slots 2129*b* of the cartridge body 2220. Also, similarly, the proximal rails 2228*c* of the staple drivers 2220 are not in contact with the proximal ends of the proximal rail slots 2128*c* of the cartridge body 2110. As a result of this arrangement, a clearance gap is present between the rails 2228*a*, 2229*b*, and 2228*c* and the ends of the rail slots 2128*a*, 2129*b*, and 2128*c*, respectively. As such, the rails 2228*a*, 2229*b*, and 2228*c* and the ends of the rail slots 2128*a*, 2129*b*, and 2128*c* do not comprise control surfaces which are part of the bearing zone 2119.

Figure 9:
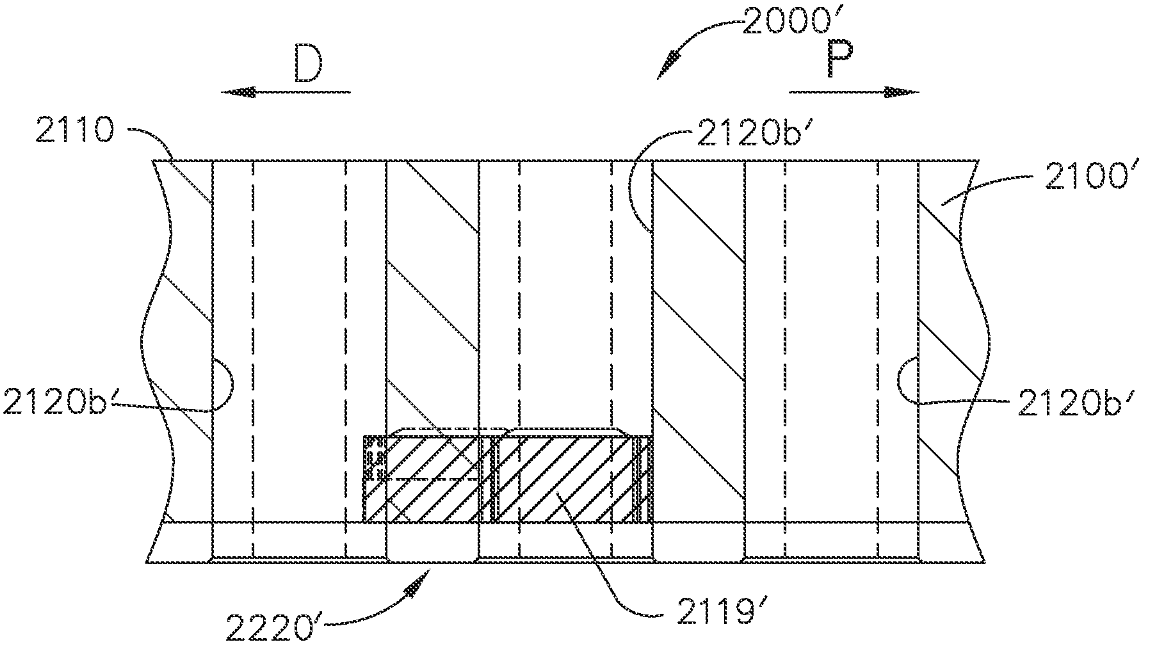
FIG. 9 is a partial cross-sectional elevational view of a staple cartridge in accordance with the present disclosure.

Notably, further to the above, the bearing zone 2119 does not extend the entire longitudinal length of the staple driver 2220. By way of comparison, referring to FIG. 9 which depicts a cartridge body 2100', the staple cavities of the cartridge body 2100', including the staple cavities 2120*b*', define a bearing zone 2119' (represented by a cross-hatched area) between each staple driver 2220' and the cartridge body 2210' that extends along the entire length of the staple driver 2220'. The bearing zone 2119 is compact as compared to the bearing zone 2119'. In accordance with the present disclosure, the longitudinal length of the bearing zone 2119 may be less than half of the longitudinal length of the staple driver 2220. Alternatively, the longitudinal length of the bearing zone 2119 may be less than one third of the longitudinal length of the staple driver 2220. Alternatively, the longitudinal length of the bearing zone 2119 may be less than one quarter of the longitudinal length of the staple driver 2220. Alternatively, the longitudinal length of the bearing zone 2119 may be less than one fifth of the longitudinal length of the staple driver 2220. Given the shorter longitudinal length of the bearing zone 2119 as compared to the bearing zone 2119', the force needed to fire the staple drivers 2220 may be less than the force needed to fire the staple drivers 2220' thereby resulting in less force needed to push the sled 2230 distally during the staple firing stroke.

As discussed above, referring again to FIG. 5, the staple drivers 2220 ride up the ramps 2232 of the sled 2230 within the staple cavities 2120 as the sled 2230 passes thereunder. More specifically, as also discussed above, the ramp surfaces 2222 of the staple drivers 2220 slide up the ramps 2232 of the sled 2230 until the staple drivers 2220 reach the tops of the ramps 2232. At such point, as also discussed above, the staples 2240 being deformed by the staple drivers 2220 are deformed to their fully-deformed configurations. However, a staple driver 2220 may rotate distally, or roll forward, when the sled 2230 contacts the staple driver 2220 during the staple firing stroke. The proximal end of the staple driver 2220 may lift above the distal end of the staple driver 2220. Such rotation, or rolling, of the staple driver 2220 can increase the force needed to lift the staple driver 2220. The contact interfaces between the guide rails 2229*a*, 2228*b*, and 2229*c* and the guide rail slots 2129*a*, 2128*b*, and 2129*c*, respectively, as discussed above, can reduce, if not prevent, the rolling of the staple drivers 2220. The guide rails 2229*a*, 2228*b*, and 2229*c* can co-operatively grip the cartridge body 2100 to resist the rolling of the staple drivers 2220. As the sled 2230 passes by a staple driver 2220 that has just been lifted to its fully-fired position, the staple driver 2220 becomes unsupported by the sled 2230. The staple driver 2220 can rotate proximally, or rock back, as the sled 2230 loses contact with the staple driver 2220. Stated another way, the proximal end of the staple driver 2220 can fall below the distal end. As above, the contact interfaces between the guide rails 2229*a*, 2228*b*, and 2229*c* and the guide rail slots 2129*a*, 2128*b*, and 2129*c*, respectively, can reduce, if not prevent, the rocking of the staple drivers 2220.

Referring again to FIG. 5, each ramp 2232 of the sled 2230 comprises a first, or distal, ramp portion 2232*d* extending at a first angle and a second, or proximal, ramp portion 2232*p* extending at a second angle that is different than the first angle. The first angle is steeper than the second angle when measured from a plane B defined by the bottom of the sled 2230. As a result, the staple driver 2220 is lifted quickly on the first ramp portion 2232*d* and then slowly, or slower, on the second ramp portion 2232*p*-assuming that the longitudinal translational speed of the sled 2230 remains constant. The staples 2240 are not in contact with the anvil 3320 while the staple drivers 2220 are being lifted by the distal ramp portions 2232*d* and, as a result, the staple drivers 2230 do not experience high loads while being lifted quickly by the distal ramp portions 2232*d*. The staples 2240 come into contact with the anvil 3320 while being lifted by the proximal ramp portions 2232*p* which creates higher firing loads in the staple drivers 2230. The slower lifting rate of the staple drivers 2220 can be conducive to good staple formation. The ramp surfaces 2222 of the staple drivers 2220 are defined by an angle that matches the second angle of the ramps 2232. As a result, the ramp surfaces 2222 sit flush, or at least substantially flush, on the second ramp portions 2232*p* of the sled ramps 2232 where the staple drivers 2220 experience higher firing loads. Correspondingly, the sled ramps 2232 do not sit flush on the first ramp portions 2232*d* of the sled ramps 2232 where the staple drivers 2220 experience lower firing loads. The above being said, other embodiments are envisioned in which the sled ramps 2232 are defined by a constant angle and the ramp surfaces 2222 on the staple drivers 2220 extend at the same angle as the sled ramps 2232. The sled ramps 2232 can be defined by one or more arcuate surfaces.

The above being said, sled ramps having shallow ramp angles and sled ramps having steep ramp angles have both advantages and disadvantages. As discussed above, sled ramps having shallow ramp angles may lift the staple drivers more slowly which can result in better staple formation as compared to sled rails having steeper ramp angles. That said, sled ramps having shallow ramp angles will be longitudinally longer than sled ramps having steeper ramp angles which can require longer end effectors of the stapling instrument to house the sled. Stapling instruments having shorter end effectors may be better suited to fit within smaller spaces within the patient than longer end effectors. Correspondingly, sled ramps having steeper ramp angles may lift staple drivers more quickly and may require shorter end effectors of the stapling instruments; however, such steeper ramp angles may more readily induce forward rolling in the staple drivers during the staple firing stroke. Accordingly, finding a balance between these considerations can produce desirable results and various embodiments discussed below comprise improvements that can be used to offset one or more of these issues.

Figure 11:
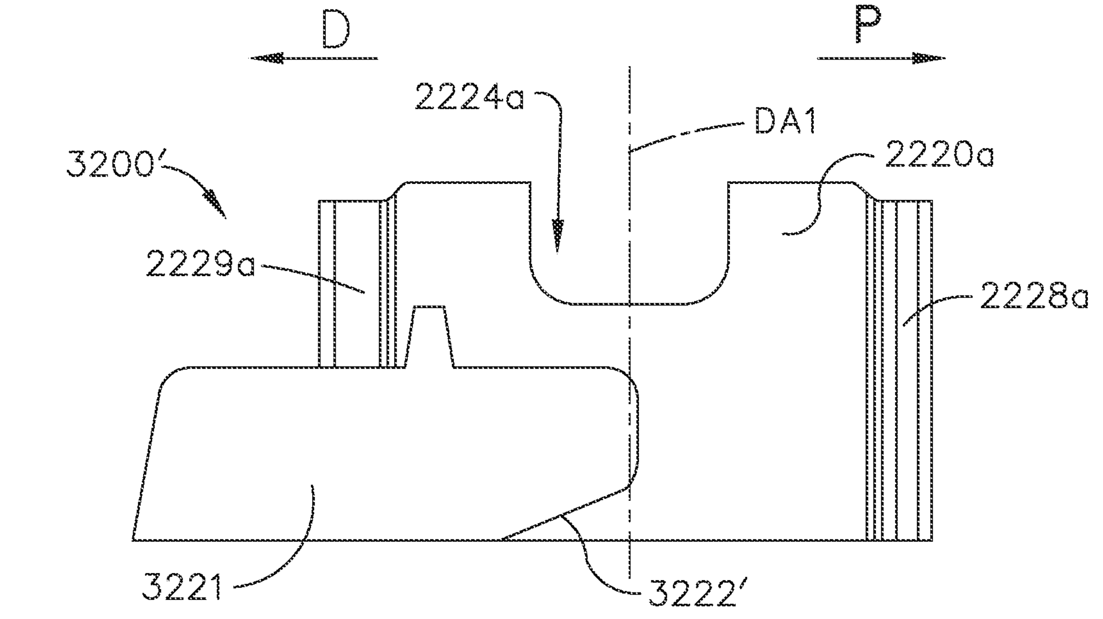
FIG. 11 is a cross-sectional elevational view of a staple driver in accordance with the present disclosure.
Figure 10:
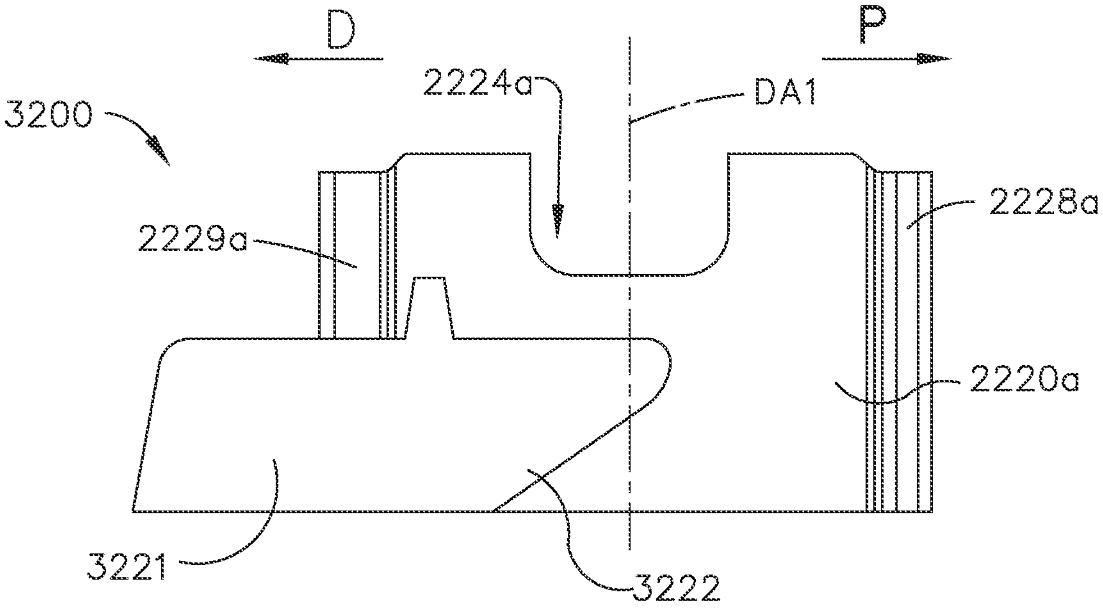
FIG. 10 is a cross-sectional elevational view of a staple driver in accordance with the present disclosure.

When the staple driver 2220 is lifted upwardly by the sled 2230, further to the above, the first driver pillar 2220*a* is driven along a first vertical drive axis, the second drive pillar 2220*b* is driven along a second vertical drive axis, and the third drive pillar 2220*c* is driven along a third vertical drive axis. Turning now to FIG. 10, a staple driver 3200 comprises a first drive pillar 2220*a*, a second drive pillar 2220*b*, and a third drive pillar 2220*c* in the same arrangement as the staple driver 2220. Notably, though, only the first drive pillar 2220*a* is depicted in FIG. 10. Also, notably, a first vertical drive axis DA1 extends through the middle, or center, of the first drive pillar 2220*a* and the cradle 2224*a* defined on the top thereof. The staple driver 3200 further comprises two connectors 3221—one connector 3221 that connects the first driver pillar 2220*a* and the second drive pillar 2220*b* and one connector 3221 that connects the second drive pillar 2220*b* and the third drive pillar 2220*c*. Each connector 3221 comprises a proximally-facing ramp surface 3222 that is configured to be engaged by a ramp of a sled during a staple firing stroke. By way of comparison, referring to FIG. 11, a staple driver 3200' is the same as the staple driver 3200 except for the ramp surfaces 3222' on the connectors 3221. Among other differences, the ramp surfaces 3222' have a shallower angle—which correspond to the shallower ramps of a sled—than the ramp surfaces 3222 which correspond the steeper ramps of a different sled. Further to the above, the steeper ramp surfaces 3222 of the staple driver 3220 may, absent more, tend to cause more forward roll than the shallower ramp surfaces 3222' of the staple driver 3220'. To address this issue, and reduce the potential forward roll of the staple driver 3220, the ramp surfaces 3222 of the staple driver 3220 extend further proximally than the ramp surfaces 3222'. As illustrated in FIG. 10, the ramp surfaces 3222 extend proximally relative to the first drive axis DA1. Moreover, although not illustrated, the third drive pillar 2220*c* of the staple driver 3220 is aligned laterally with the first drive pillar 2220*a* and the third drive axis DA3 is aligned laterally with the first drive axis DA1. As such, in this embodiment, the ramp surfaces 3222 also extend proximally relative to third drive axis DA3.

Figure 2A:
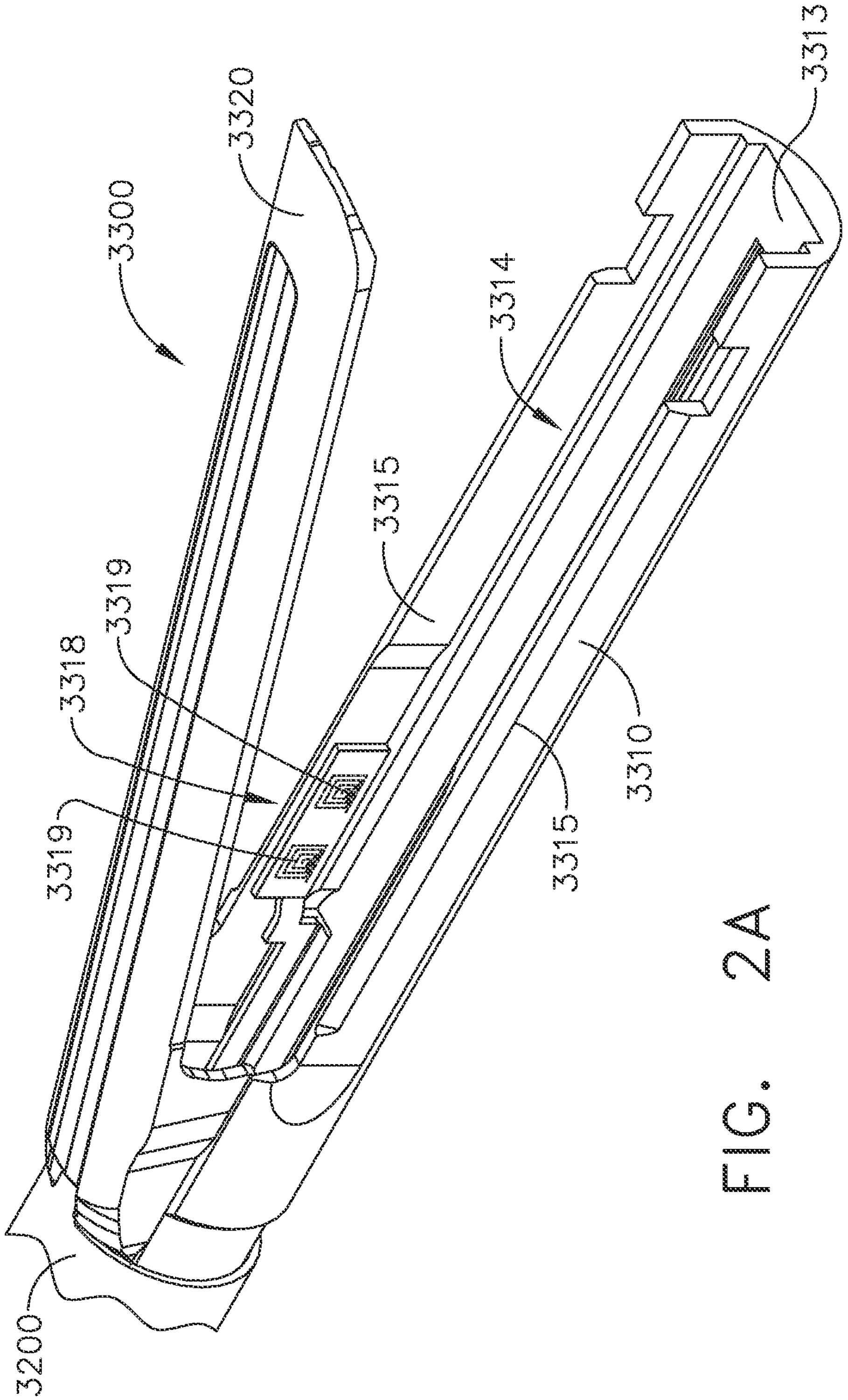
FIG. 2A is a perspective view of the end effector of FIG. 1 without the replaceable staple cartridge.

Referring again to FIGS. 2 and 2A, the staple cartridge 2000 comprises a cartridge circuit 2318 that is placed in communication with a channel jaw circuit 3318 of the cartridge jaw 3310 when the staple cartridge 2000 is seated in the cartridge jaw 3310. The cartridge circuit 2318 comprises contacts 2319 that engage contacts 3319 of the channel jaw circuit 3318.

Figure 12:
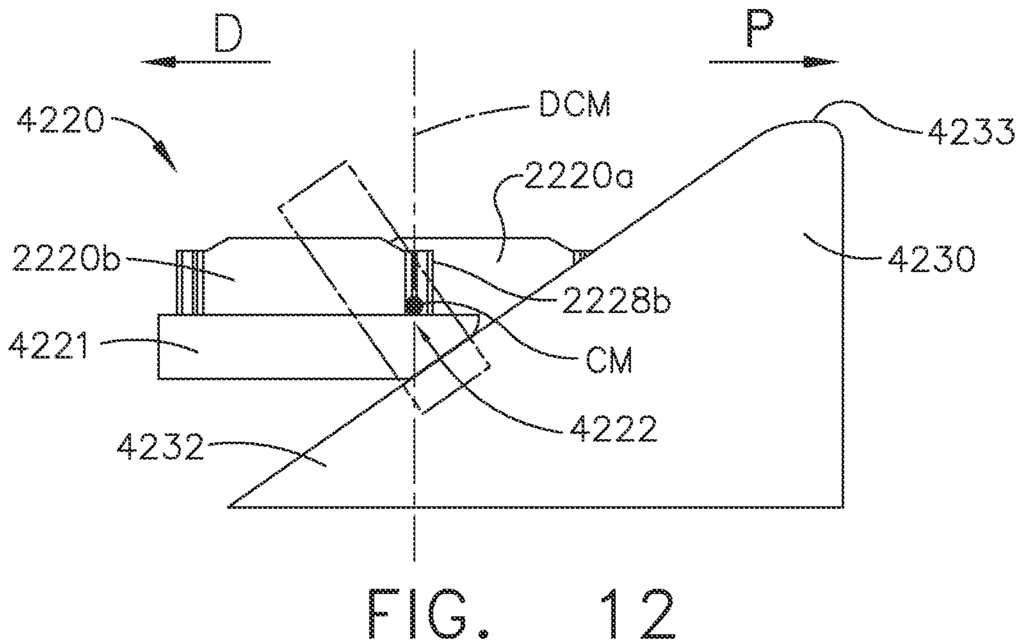
FIG. 12 is a cross-sectional elevational view of a staple driver being lifted by a sled in accordance with the present disclosure.

Referring now to FIG. 12, a sled 4230 is depicted lifting a staple driver 4220 during a staple firing stroke. Similar to the sled 2230, the sled 4230 comprises ramps 4232 that are configured to engage two ramp surfaces 4222 defined on the staple driver 4220. Each of the sled ramps 4232 comprises an apex 4323 which represents the fully-fired position of the staple driver 4220. Similar to the staple driver 2220, the staple driver 4220 comprises a first drive pillar 2220*a* and a second drive pillar 2220*b* and, although not illustrated, a third drive pillar 2220*c* arranged in the same manner as the staple driver 2220. The staple driver 4220 further comprises two connectors 4221—each having one of the ramp surfaces 4222. Also similar to the staple driver 2220, one connector 4221 connects the first drive pillar 2220*a* and the second drive pillar 2220*b* and the other connector 4221 connects the second drive pillar 2220*b* and the third drive pillar 2220*c*.

Figure 13:
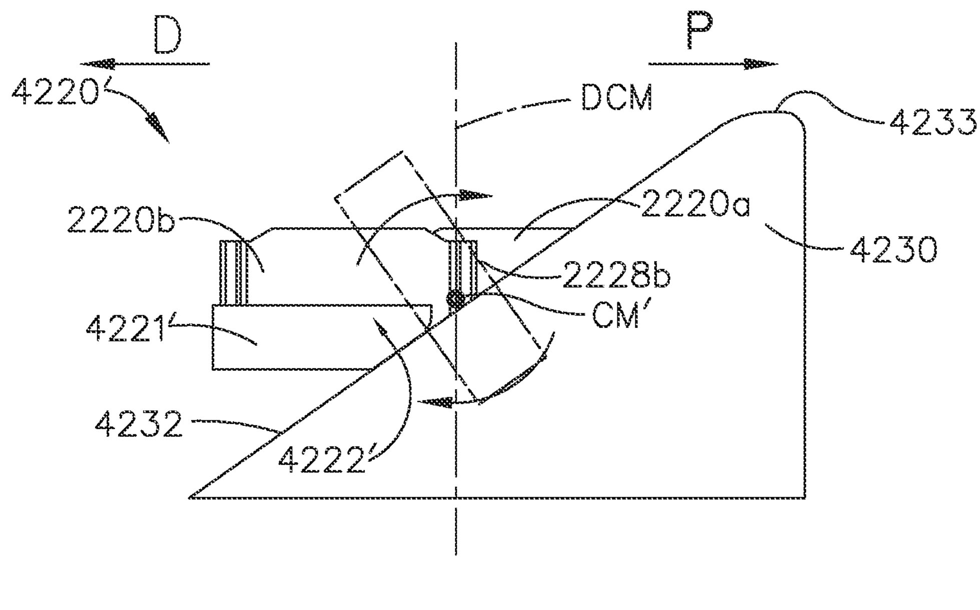
FIG. 13 is a cross-sectional elevational view of a staple driver being lifted by a sled in accordance with the present disclosure.

Notably, the connectors 4221 and the ramp surfaces 4222 of the staple driver 4220 extend proximally relative to the center of mass CM of the staple driver 4220. As a result of the ramp surfaces 4222 extending at least partially proximally relative to the center of mass CM, the staple driver 4220 is less likely to roll forward when being lifted during the staple firing stroke. The entirety of the ramp surfaces 4222 may extend proximally relative to the center of mass CM. By way of comparison, referring to FIG. 13, a staple driver 4220' comprises connectors 4221' and ramp surfaces 4222' that do not extend proximally with respect to the center of mass (CM') of the staple driver 4220'. As a result, the staple driver 4220' may tend to roll forward as compared to the staple driver 4220. Moreover, the ramp surfaces 4222 of the staple drivers 4220 at least partially extend proximally relative to the second drive pillar 4220*b*. The ramp surfaces 4222 may extend at least partially proximally relative to the proximal guide rail 2228*b* of the staple driver 4220. The entirety of the ramp surfaces 4222 may extend proximally relative to the second drive pillar 4220*b* and/or the proximal guide rail 2228*b* of the staple driver 4220. Such embodiments, similar to the above, can reduce the tendency of the staple driver 4200 to roll forward while being lifted by a sled during the staple firing stroke.

Figure 14:
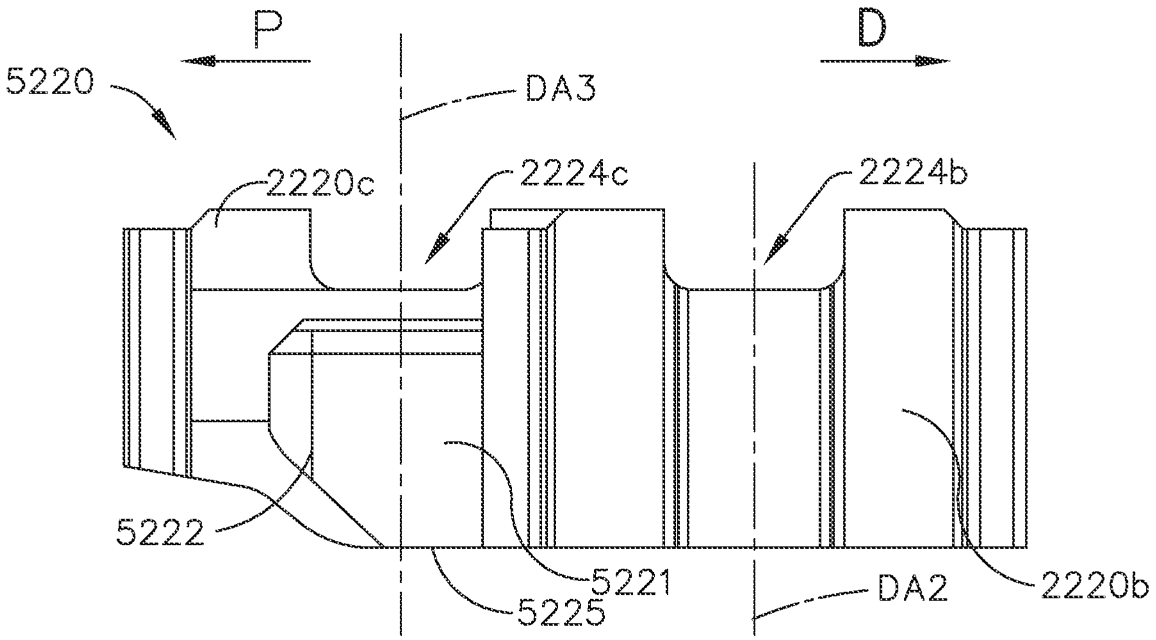
FIG. 14 is an elevational view of a staple driver in accordance with the present disclosure.
Figure 15:
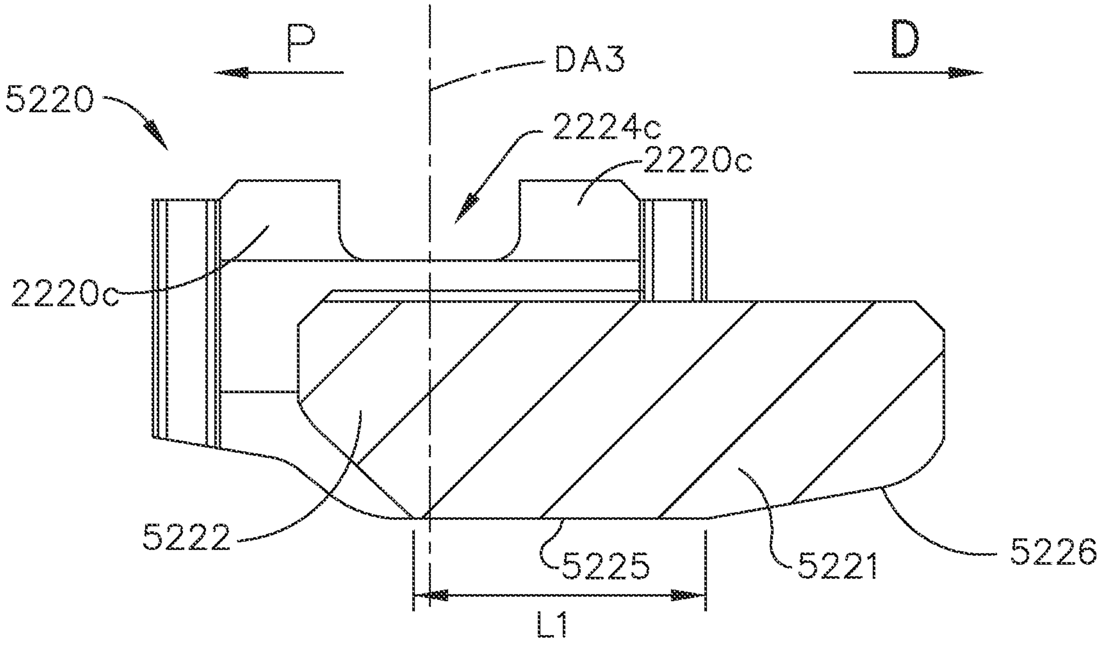
FIG. 15 is a cross-sectional view of the staple driver of FIG. 14.

As discussed above, a staple driver may rotate proximally, or rock back, when the staple driver reaches the top, or apex, of the sled ramps. As discussed below, referring to FIGS. 14 and 15, a staple driver 5220 comprises one or more features that can prevent, or at least reduce, such rocking. Like the staple driver 2220, the staple driver 5220 comprises a first drive pillar 2220*a* (not illustrated), a second drive pillar 2220*b*, and a third drive pillar 2220*c*. Further to the above, the second drive pillar 2220*b* moves along a second drive axis DA2. Notably, the second drive axis DA2 extends through the middle, or center, of the drive pillar 2220*b* and the cradle 2224*b* defined thereon. Similarly, the third drive pillar 2220*c* moves along a third drive axis DA3 which extends through the middle, or center, of the third drive pillar 2220*c* and the cradle 2224*c*. Similar to the staple driver 2220, the staple driver 5220 comprises two connectors 5221—one connector 5221 that connects the first drive pillar 2220*a* and the second drive pillar 2220*b* and one connector 5221 that connects the second drive pillar 2220*b* and the third drive pillar 2220*c*. Each connector 5221 comprises a proximal-facing ramp surface 5222 that is engaged by a sled ramp during a staple firing stroke to lift the staple driver 5220 upwardly within a staple cavity 2120. Each connector 5221 further comprises a driver hold surface 5225 extending distally from the ramp surface 5222 and a distal-facing fall-off ramp 5226 extending distally from the driver hold surface 5225. The drive hold surface 5225 comprises a flat surface, but can comprise any suitable configuration. Once the sled rail has lifted the staple driver 5220 to its fully-fired position, the apex of the sled rail slides along the flat 5225 which holds the staples 2240 already deformed by the staple driver 5220 against the anvil 3320. As the sled continues further distally during the staple firing stroke, the apex of the sled rail passes under the fall-off ramp 5226 of the staple driver 5220. The staple driver 5220 can move downwardly to relieve the pressure on the stapled tissue.

Figure 16:
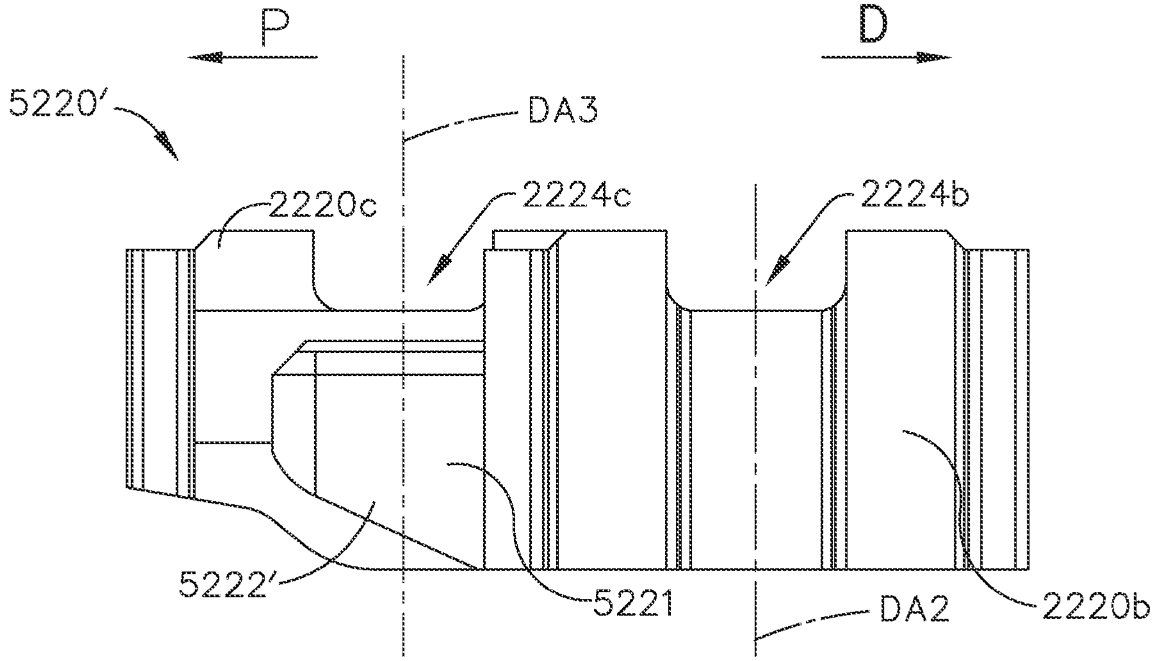
FIG. 16 is an elevational view of a staple driver in accordance with the present disclosure.
Figure 17:
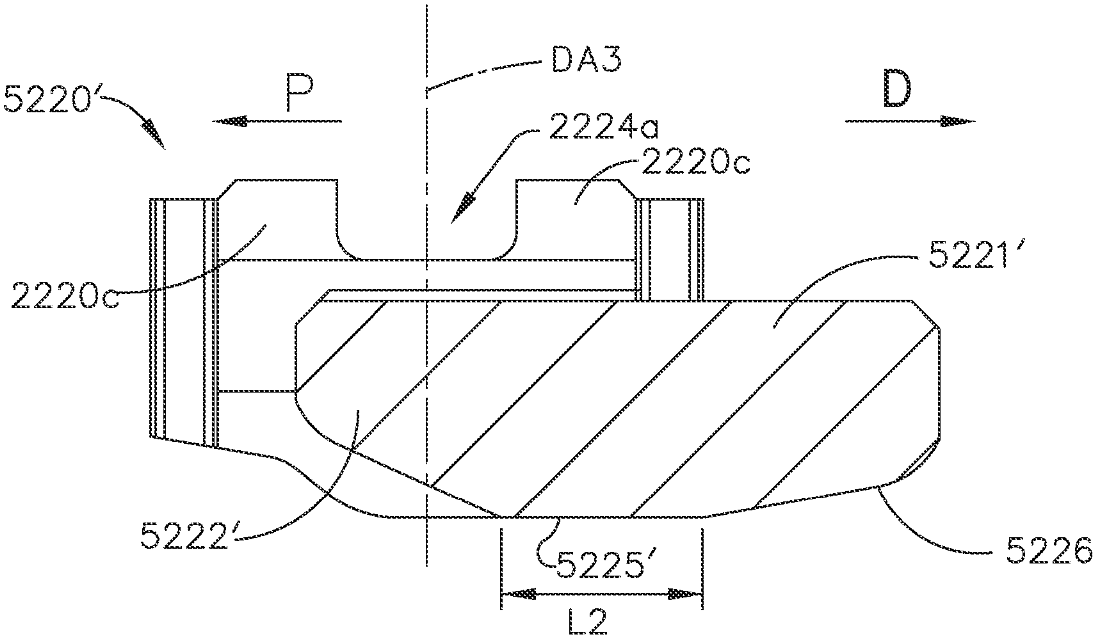
FIG. 17 is a cross-sectional view of the staple driver of FIG. 16.

Further to the above, the staple driver 5220 can, absent more, rock backward, or proximally, when the sled rail is engaged with the flat 5225 of the staple driver 5220. When a staple driver rocks back, all of the staples being deformed by a staple driver may not be deformed to a desired formed height if the staple driver rocks backward. To reduce the possibility of such rocking, or the amount of such rocking, the length L1 of the flat 5225, and the position of the flat 5225, are such that the staple driver 5220 has a stable interface with the apex of the sled ramps. Notably, referring to FIG. 15, the flat 5225 extends proximally relative to the third drive axis DA3 of the third drive pillar 2220*c* of the staple driver 5220. Although not illustrated, the first drive pillar 2220*a* of the staple driver 5220 is aligned laterally with the third drive pillar 2220*c* such that the first drive axis DA1 of the first drive pillar 2220*a* is aligned laterally with the third drive axis DA3. Thus, the flat 5225 of the staple driver 5220 extends proximally relative to the first drive axis DA1 as well. Owing to this arrangement, the staple driver 5220 is less likely to rock backward during a staple firing stroke. By way of comparison, referring to FIGS. 16 and 17, a flat 5225' defined on a connector 5221' of a staple driver 5220' has a length L2 that is shorter than the flat 5225 of the staple driver 5220 and does not extend proximally relative to the first drive axis DA1 and third drive axis DA3 of the first and third drive pillars 2220*a* and 2220*c*, respectively.

Further to the above, a sled, or at least a portion of a sled, can be retracted proximally after a staple firing stroke. The sled may come into contact with the staple drivers 5220 as the sled is being retracted, especially if the staple drivers 5220 have fallen down within their staple cavities behind the sled after the sled has passed thereby during the staple firing stroke. The distal-facing ramps 5226 can assist in re-lifting the staple drivers 5220 into their fired positions as the sled is retracted proximally.

Many of the surgical instrument systems described herein are motivated by an electric motor; however, the surgical instrument systems described herein can be motivated in any suitable manner. The surgical instrument systems described herein can be motivated by a manually-operated trigger, for example. The motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector can comprise electrodes configured to heat and seal the tissue. Also, for instance, an end effector can apply vibrational energy to seal the tissue.

Various aspects of the subject matter described herein are set out in the following examples.

1. A staple cartridge comprising a cartridge body comprising a proximal end, a distal end, a longitudinal axis extending between said proximal end and said distal end, a first longitudinal row of staple cavities comprising a first staple cavity, wherein said first staple cavity comprises a first proximal cavity end and a first distal cavity end, and a second longitudinal row of staple cavities comprising a second staple cavity, wherein said second staple cavity comprises a second proximal cavity end and a second distal cavity end. The staple cartridge a first staple removably stored in said first staple cavity, a second staple removably stored in said second staple cavity, and a staple driver, comprising a first drive pillar comprising a first seat, wherein said first drive pillar is translatable within said first staple cavity during a staple firing stroke, wherein said first drive pillar is configured to drive said first staple during said staple firing stroke, and wherein said first drive pillar comprises a first distal driver end, and a second drive pillar comprising a second seat, wherein said second drive pillar is translatable within said second staple cavity during said staple firing stroke, wherein said second drive pillar is configured to drive said second staple during said staple firing stroke, wherein said second drive pillar comprises a second proximal driver end, and wherein said first distal driver end of said first drive pillar and said second proximal driver end of said second drive pillar are engaged with said cartridge body to inhibit the rotation of said staple driver relative to said cartridge body.

2. The staple cartridge of Example 1, wherein said first distal driver end of said first drive pillar and said second proximal driver end of said second drive pillar co-operatively grip said cartridge body to inhibit the rotation of said staple driver relative to said cartridge body.

3. The staple cartridge of Example 1 or 2, wherein said staple driver further comprises a connector connecting said first drive pillar and said second drive pillar, and wherein said connector comprises a flexible region that permits said first drive pillar and said second drive pillar to grip said cartridge body.

4. The staple cartridge of Example 1, 2, or 3, wherein said first drive pillar further comprises a first proximal driver end, wherein said second drive pillar further comprises a second distal driver end, and wherein said first proximal driver end and said second distal driver end are not engaged with said cartridge body.

5. The staple cartridge of Example 1, 2, 3, or 4, wherein said cartridge body further comprises a third longitudinal row of staple cavities comprising a third staple cavity, wherein said third staple cavity comprises a third proximal cavity end and a third distal cavity end, wherein said staple cartridge further comprises a third staple removably stored in said third staple cavity, wherein said staple driver further comprises a third drive pillar comprising a third distal driver end and a third drive seat, wherein said third drive pillar is translatable within said third staple cavity to drive said third staple during said staple firing stroke, and wherein said third distal driver end is engaged with said cartridge body to inhibit the rotation of said staple driver relative to said cartridge body.

6. The staple cartridge of Example 5, wherein said second longitudinal row of staple cavities is positioned intermediate said first longitudinal row of staple cavities and said third longitudinal row of staple cavities.

7. The staple cartridge of Example 5 or 6, wherein said third drive pillar comprises a third proximal driver end, and wherein said third proximal driver end is not engaged with said cartridge body.

8. A staple cartridge comprising a cartridge body comprising a proximal end, a distal end, a longitudinal axis extending between said proximal end and said distal end, a deck configured to support patient tissue, a first longitudinal row of staple cavities comprising first staple cavities defined in said deck, and a second longitudinal row of staple cavities comprising second staple cavities defined in said deck. The staple cartridge further comprises a plurality of first staples removably stored in said first longitudinal row of first staple cavities, a plurality of second staples removably stored in said second longitudinal row of second staple cavities, a longitudinal row of staple drivers comprising a first staple driver translatable within a said first staple cavity and a said second staple cavity and a second staple driver translatable within a said first staple cavity and a said second staple cavity, wherein said first staple driver is positioned proximally with respect to said second staple driver, and a sled configured to lift said first staple driver from an unlifted position to a lifted position during a staple firing stroke, wherein said first staple driver is in contact with said cartridge body and said second staple driver when said first staple driver is in said lifted position.

9. The staple cartridge of Example 8, wherein said first staple driver comprises a first drive pillar that is configured to translate within a said first staple cavity and a second drive pillar that is configured to translate within a said second staple cavity during said staple firing stroke, wherein said first drive pillar comprises a first seat configured to drive a said first staple and said second drive pillar comprises a second seat configured to drive a said second staple during said staple firing stroke, wherein said first drive pillar is engaged with said cartridge body when said first staple driver is in said lifted position, and wherein said second drive pillar is engaged with said second staple driver when said first staple driver is in said lifted position.

10. The staple cartridge of Example 9, wherein said first drive pillar is engaged with said cartridge body and said second drive pillar is engaged with said second staple driver when said first staple driver is in said unlifted position.

11. The staple cartridge of Example 9, wherein said second drive pillar is not engaged with said second staple driver when said first staple driver is in said unlifted position.

12. The staple cartridge of Example 8, 9, 10, or 11, wherein said cartridge body further comprises a third longitudinal row of staple cavities comprising third staple cavities defined in said deck, wherein said staple cartridge further comprises a third plurality of staples removably stored in said third longitudinal row of staple cavities, wherein said first staple driver further comprises a third drive pillar that is configured to translate within a said third staple cavity during said staple firing stroke, wherein said third drive pillar comprises a third seat configured to drive a said third staple during said staple firing stroke, and wherein said third drive pillar is engaged with said cartridge body when said first staple driver is in said lifted position.

13. The staple cartridge of Example 12, wherein said second driver pillar is positioned intermediate said first drive pillar and said third drive pillar.

14. The staple cartridge of Example 8, 9, 10, or 11, wherein said cartridge body further comprises a third longitudinal row of staple cavities comprising third staple cavities defined in said deck, wherein said staple cartridge further comprises a third plurality of staples removably stored in said third longitudinal row of staple cavities, wherein said first staple driver further comprises a third drive pillar that is configured to translate within a said third staple cavity during said staple firing stroke, wherein said third drive pillar comprises a third seat configured to drive a said third staple during said staple firing stroke, and wherein said third drive pillar is engaged with said second staple driver when said first staple driver is in said lifted position.

15. The staple cartridge of Example 14, wherein said second driver pillar is positioned intermediate said first drive pillar and said third drive pillar.

16. A staple cartridge comprising a cartridge body comprising a proximal end, a distal end, a longitudinal axis extending between said proximal end and said distal end, a deck configured to support patient tissue, a first longitudinal row of staple cavities comprising first staple cavities defined in said deck, and a second longitudinal row of staple cavities comprising second staple cavities defined in said deck. The staple cartridge further comprises a plurality of first staples removably stored in said first longitudinal row of staple cavities, a plurality of second staples removably stored in said second longitudinal row of staple cavities, and a staple driver comprising a first drive pillar translatable within a said first staple cavity, a second drive pillar translatable with a said second staple cavity, wherein said second drive pillar extends distally relative to said first drive pillar, a connector connecting said first drive pillar and said second drive pillar, wherein said connector comprises a cam surface, and a center of mass. The staple cartridge further comprises a sled configured to engage said cam surface of said staple driver and lift said staple driver toward said deck during a staple firing stroke, wherein said cam surface extends proximally relative to said center of mass of said staple driver.

17. The staple cartridge of Example 16, wherein the entirety of said cam surface extends proximally relative to said center of mass of said staple driver.

18. The staple cartridge of Example 16 or 17, wherein said first drive pillar comprises a first proximal driver end, a first distal driver end, and a first drive axis centered between said first proximal driver end and said first distal driver end, wherein said second drive pillar comprises a second proximal driver end, a second distal driver end, and a second drive axis centered between said second proximal driver end and said second distal driver end, and wherein said cam surface extends proximally relative to said first drive axis and said second drive axis.

19. The staple cartridge of Example 18, wherein said cartridge body further comprises a third longitudinal row of staple cavities comprising third staple cavities defined in said deck, wherein said staple cartridge further comprises a plurality of third staples removably stored in said third longitudinal row of staple cavities, wherein said staple driver further comprises a third drive pillar translatable within a said third staple cavity and a second connector connecting said second drive pillar and said third drive pillar, wherein said third drive pillar comprises a third proximal driver end, a third distal driver end, and a third drive axis centered between said third proximal driver end and said third distal driver end, and wherein said cam surface extends proximally relative to said third drive axis.

20. The staple cartridge of Example 16, 17, or 18, wherein said cartridge body further comprises a third longitudinal row of staple cavities comprising third staple cavities defined in said deck, wherein said staple cartridge further comprises a plurality of third staples removably stored in said third longitudinal row of staple cavities, wherein said staple driver further comprises a third drive pillar translatable within a said third staple cavity and a second connector connecting said second drive pillar and said third drive pillar, wherein said second connector comprises a second cam surface, wherein said sled is configured to engage said second cam surface and lift said staple driver toward said deck during said staple firing stroke, and wherein said second cam surface extends proximally relative to said center of mass of said staple driver.

21. A staple cartridge comprising a cartridge body comprising a proximal end, a distal end, a longitudinal axis extending between said proximal end and said distal end, a deck configured to support patient tissue, a first longitudinal row of staple cavities comprising first staple cavities defined in said deck, and a second longitudinal row of staple cavities comprising second staple cavities defined in said deck. The staple cartridge further comprises a plurality of first staples removably stored in said first longitudinal row of staple cavities, a plurality of second staples removably stored in said second longitudinal row of staple cavities, and a staple driver comprising a first drive pillar translatable within a said first staple cavity, wherein said first drive pillar comprises a first distal driver end, a first proximal driver end, and a first drive axis centered between said first proximal driver end and said first distal driver end and a second drive pillar translatable within a said second staple cavity, wherein said second drive pillar comprises a second distal driver end, a second proximal driver end, and a second drive axis centered between said second proximal driver end and said second distal driver end, and wherein said second drive axis is positioned distally with respect to said first drive axis, and a connector connecting said first drive pillar and said second drive pillar, wherein said connector comprises a cam surface. The staple cartridge further comprises a sled configured to engage said cam surface of said staple driver and lift said staple driver toward said deck during a staple firing stroke, wherein said cam surface extends proximally relative to said first drive axis and said second drive axis of said staple driver.

22. The staple cartridge of Example 21, wherein said cartridge body further comprises a third longitudinal row of staple cavities comprising third staple cavities defined in said deck, wherein said staple cartridge further comprises a plurality of third staples removably stored in said third longitudinal row of staple cavities, wherein said staple driver further comprises a third drive pillar translatable within a said third staple cavity and a second connector connecting said second drive pillar and said third drive pillar, wherein said third drive pillar comprises a third proximal driver end, a third distal driver end, and a third drive axis centered between said third proximal driver end and said third distal driver end, and wherein said cam surface extends proximally relative to said third drive axis.

23. The staple cartridge of Example 22, wherein said second drive axis is positioned distally with respect to said third drive axis.

24. The staple cartridge of Example 22 or 23, wherein said second connector comprises a second cam surface, wherein said sled is configured to engage said second cam surface and lift said staple driver toward said deck during said staple firing stroke, and wherein said second cam surface extends proximally relative to said first drive axis, said second drive axis, and said third drive axis of said staple driver.

25. A staple cartridge comprising a cartridge body comprising a proximal end, a distal end, a longitudinal axis extending between said proximal end and said distal end, a deck configured to support patient tissue, a first longitudinal row of staple cavities comprising first staple cavities defined in said deck, and a second longitudinal row of staple cavities comprising second staple cavities defined in said deck. The staple cartridge further comprises a plurality of first staples removably stored in said first longitudinal row of staple cavities, a plurality of second staples removably stored in said second longitudinal row of staple cavities, and a staple driver movable from an unfired position to a fully-fired position during a staple firing stroke comprising a first drive pillar translatable within a said first staple cavity, wherein said first drive pillar comprises a first distal driver end, a first proximal driver end, and a first drive axis centered between said first proximal driver end and said first distal driver end, a second drive pillar translatable within a said second staple cavity, wherein said second drive pillar comprises a second distal driver end, a second proximal driver end, and a second drive axis centered between said second proximal driver end and said second distal driver end, and wherein said second drive axis is positioned distally with respect to said first drive axis, and a connector connecting said first drive pillar and said second drive pillar, wherein said connector comprises a proximally-facing cam surface and a driver hold surface extending distally from said proximal-facing cam surface. The staple cartridge further comprises a sled configured to engage said proximally-facing cam surface of said staple driver and lift said staple driver from said unfired position to said fully-fired position during said staple firing stroke, wherein said sled is configured to engage said driver hold surface after engaging said proximally-facing cam surface to hold said staple driver in said fully-fired position, and wherein said driver hold surface extends proximally relative to said first drive axis and said second drive axis of said staple driver.

26. The staple cartridge of Example 25, wherein said driver hold surface comprises a flat surface.

27. The staple cartridge of Example 25 or 26, wherein said connector further comprises a distally-facing fall-off ramp, and wherein said driver hold surface extends between said proximally-facing ramp and said distally-facing fall-off ramp.

28. The staple cartridge of Example 25, 26, or 27, wherein said cartridge body further comprises a third longitudinal row of staple cavities comprising third staple cavities defined in said deck, wherein said staple cartridge further comprises a plurality of third staples removably stored in said third longitudinal row of staple cavities, wherein said staple driver further comprises a third drive pillar translatable within a said third staple cavity and a second connector connecting said second drive pillar and said third drive pillar, wherein said third drive pillar comprises a third proximal driver end, a third distal driver end, and a third drive axis centered between said third proximal driver end and said third distal driver end, and wherein said driver hold surface extends proximally relative to said third drive axis.

29. The staple cartridge of Example 28, wherein said second drive axis is positioned distally with respect to said third drive axis.

30. The staple cartridge of Example 28 or 29, wherein said second connector comprises a second cam surface, wherein said sled is configured to engage said second cam surface and lift said staple driver from said unfired position to said fully-fired position during said staple firing stroke, and wherein said second cam surface extends proximally relative to said first drive axis, said second drive axis, and said third drive axis.

Various aspects of the subject matter described herein are set out in the following additional examples.

1. A staple cartridge (2000) comprising a cartridge body (2100), comprising a proximal end, a distal end, a longitudinal axis extending between said proximal end and said distal end, a first longitudinal row of staple cavities (2120*a*) comprising a first staple cavity, and a second longitudinal row of staple cavities (2120*b*) comprising a second staple cavity. The first staple cavity comprises a first proximal cavity end and a first distal cavity end. The second staple cavity comprises a second proximal cavity end and a second distal cavity end. The staple cartridge further comprises a first staple (2240) removably stored in said first staple cavity, a second staple (2240) removably stored in said second staple cavity, and a staple driver (2200) comprising a first drive pillar (2220*a*) comprising a first seat (2224*a*) and a second drive pillar (2220*b*) comprising a second seat (2224*b*). The first drive pillar is translatable within said first staple cavity during a staple firing stroke. The first drive pillar is configured to drive said first staple during said staple firing stroke. The first drive pillar comprises a first distal driver end (2229*a*). The second drive pillar is translatable within said second staple cavity during said staple firing stroke. The second drive pillar is configured to drive said second staple during said staple firing stroke. The second drive pillar comprises a second proximal driver end (2228*b*). The first distal driver end of said first drive pillar and said second proximal driver end of said second drive pillar are engaged with said cartridge body to inhibit the rotation of said staple driver relative to said cartridge body.

2. The staple cartridge of Example 1, wherein said first distal driver end (2229*a*) of said first drive pillar (2220*a*) and said second proximal driver end (2228*b*) of said second drive pillar (2220*b*) co-operatively grip said cartridge body (2100) to inhibit the rotation of said staple driver (2200) relative to said cartridge body.

3. The staple cartridge of Examples 1 or 2, wherein said staple driver (2200) further comprises a connector (2221) connecting said first drive pillar (2220*a*) and said second drive pillar (2220*b*). The connector comprises a flexible region that permits said first drive pillar and said second drive pillar to grip said cartridge body (2100).

4. The staple cartridge of Examples 1, 2, or 3, wherein said first drive pillar (2220*a*) further comprises a first proximal driver end (2228*a*). The second drive pillar further comprises a second distal driver end (2229*b*). The first proximal driver end and said second distal driver end are not engaged with said cartridge body (2100).

5. The staple cartridge of Examples 1, 2, 3, or 4, wherein said cartridge body (2100) further comprises a third longitudinal row of staple cavities (2120*c*) comprising a third staple cavity. The third staple cavity comprises a third proximal cavity end (2128*c*) and a third distal cavity end (2129*c*). The staple cartridge further comprises a third staple (2240) removably stored in said third staple cavity. The staple driver (2200) further comprises a third drive pillar (2220*c*) comprising a third distal driver end (2229*c*) and a third drive seat (2224*c*). The third drive pillar is translatable within said third staple cavity to drive said third staple during said staple firing stroke. The third distal driver end is engaged with said cartridge body to inhibit the rotation of said staple driver relative to said cartridge body.

6. The staple cartridge of Example 5, wherein said second longitudinal row of staple cavities (2120*b*) is positioned intermediate said first longitudinal row of staple cavities (2120*a*) and said third longitudinal row of staple cavities (2120*c*).

7. The staple cartridge of Examples 5 or 6, wherein said third drive pillar (2220*c*) comprises a third proximal driver end (2228*c*). The third proximal driver end is not engaged with said cartridge body (2100).

8. A staple cartridge (2000) comprising a cartridge body (2100) comprising a proximal end, a distal end, a longitudinal axis extending between said proximal end and said distal end, a deck (2110) configured to support patient tissue, a first longitudinal row of staple cavities (2120*a*) comprising first staple cavities defined in said deck, and a second longitudinal row of staple cavities (2120*b*) comprising second staple cavities defined in said deck. The staple cartridge further comprises a plurality of first staples (2240) removably stored in said first longitudinal row of first staple cavities, a plurality of second staples (2240) removably stored in said second longitudinal row of second staple cavities, a longitudinal row of staple drivers (2200), and a sled (2230) configured to lift said first staple driver from an unlifted position to a lifted position during a staple firing stroke. The longitudinal row of staple drivers comprises a first staple driver translatable within a said first staple cavity and a said second staple cavity and a second staple driver translatable within a said first staple cavity and a said second staple cavity. The first staple driver is positioned proximally with respect to said second staple driver. The first staple driver is in contact with said cartridge body and said second staple driver when said first staple driver is in said lifted position.

9. The staple cartridge of Example 8, wherein said first staple driver (2200) comprises a first drive pillar (2220*a*) that is configured to translate within a said first staple cavity (2120*a*) and a second drive pillar (2220*b*) that is configured to translate within a said second staple cavity (2120*b*) during said staple firing stroke. The first drive pillar comprises a first seat (2224*a*) configured to drive a said first staple (2240) and said second drive pillar comprises a second seat (2224*b*) configured to drive a said second staple (2240) during said staple firing stroke. The first drive pillar is engaged with said cartridge body (2100) when said first staple driver is in said lifted position. The second drive pillar is engaged with said second staple driver (2200) when said first staple driver is in said lifted position.

10. The staple cartridge of Example 9, wherein said first drive pillar (2220*a*) is engaged with said cartridge body (2100) and said second drive pillar (2220*b*) is engaged with said second staple driver (2200) when said first staple driver (2200) is in said unlifted position.

11. The staple cartridge of Example 9, wherein said second drive pillar (2220*b*) is not engaged with said second staple driver (2200) when said first staple driver (2200) is in said unlifted position.

12. The staple cartridge of Examples 8, 9, 10, or 11, wherein said cartridge body (2100) further comprises a third longitudinal row of staple cavities comprising third staple cavities (2120*c*) defined in said deck (2110). The staple cartridge (2000) further comprises a third plurality of staples (2240) removably stored in said third longitudinal row of staple cavities. The first staple driver (2200) further comprises a third drive pillar (2220*c*) that is configured to translate within a said third staple cavity during said staple firing stroke. The third drive pillar comprises a third seat (2224*c*) configured to drive a said third staple during said staple firing stroke. The third drive pillar is engaged with said cartridge body when said first staple driver is in said lifted position.

13. The staple cartridge of Example 12, wherein said second driver pillar (2220*b*) is positioned intermediate said first drive pillar (2220*a*) and said third drive pillar (2220*c*).

14. The staple cartridge of Examples 8, 9, 10, or 11, wherein said cartridge body (2100) further comprises a third longitudinal row of staple cavities comprising third staple cavities (2120*c*) defined in said deck (2110). The staple cartridge (2000) further comprises a third plurality of staples (2240) removably stored in said third longitudinal row of staple cavities. The first staple driver (2200) further comprises a third drive pillar (2220*c*) that is configured to translate within a said third staple cavity during said staple firing stroke. The third drive pillar comprises a third seat (2224*c*) configured to drive a said third staple during said staple firing stroke. The third drive pillar is engaged with said second staple driver (2200) when said first staple driver is in said lifted position.

15. The staple cartridge of Example 14, wherein said second driver pillar (2220*b*) is positioned intermediate said first drive pillar (2220*a*) and said third drive pillar (2220*c*).

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STA- PLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on April 12, 22022/0022, U.S. Pat. No. 10,898,183, entitled ROBOTIC SURGICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled SURGICAL FASTENER APPLYING APPARATUS, which published on Sep. 1, 2016, U.S. Design Pat. No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A staple cartridge, comprising:

a cartridge body, comprising:

- a proximal end;
- a distal end;
- a longitudinal axis extending between said proximal end and said distal end;
- a first longitudinal row of staple cavities comprising a first staple cavity, wherein said first staple cavity comprises a first proximal cavity end and a first distal cavity end; and a second longitudinal row of staple cavities comprising a second staple cavity, wherein said second staple cavity comprises a second proximal cavity end and a second distal cavity end;

a first staple removably stored in said first staple cavity;

a second staple removably stored in said second staple cavity; and a staple driver, comprising:

a first drive pillar comprising a first seat, wherein said first drive pillar is translatable within said first staple cavity during a staple firing stroke, wherein said first drive pillar is configured to drive said first staple during said staple firing stroke, and wherein said first drive pillar comprises a first distal driver end and a first proximal driver end; and a second drive pillar comprising a second seat, wherein said second drive pillar is translatable within said second staple cavity during said staple firing stroke, wherein said second drive pillar is configured to drive said second staple during said staple firing stroke, wherein said second drive pillar comprises a second distal driver end and a second proximal driver end, wherein said first distal driver end of said first drive pillar and said second proximal driver end of said second drive pillar are engaged with said cartridge body to inhibit rotation of said staple driver relative to said cartridge body, and wherein said first proximal driver end and said second distal driver end are not engaged with said cartridge body.

2. The staple cartridge of claim 1, wherein said first distal driver end of said first drive pillar and said second proximal driver end of said second drive pillar co-operatively grip said cartridge body to inhibit the rotation of said staple driver relative to said cartridge body.

3. The staple cartridge of claim 1, wherein said staple driver further comprises a connector connecting said first drive pillar and said second drive pillar, and wherein said connector comprises a flexible region that permits said first drive pillar and said second drive pillar to grip said cartridge body.

4. The staple cartridge of claim 1, wherein said cartridge body further comprises a third longitudinal row of staple cavities comprising a third staple cavity, wherein said third staple cavity comprises a third proximal cavity end and a third distal cavity end, wherein said staple cartridge further comprises a third staple removably stored in said third staple cavity, wherein said staple driver further comprises a third drive pillar comprising a third distal driver end and a third seat, wherein said third drive pillar is translatable within said third staple cavity to drive said third staple during said staple firing stroke, and wherein said third distal driver end is engaged with said cartridge body to inhibit the rotation of said staple driver relative to said cartridge body.

5. The staple cartridge of claim 4, wherein said second longitudinal row of staple cavities is positioned intermediate said first longitudinal row of staple cavities and said third longitudinal row of staple cavities.

6. The staple cartridge of claim 4, wherein said third drive pillar comprises a third proximal driver end, and wherein said third proximal driver end is not engaged with said cartridge body.

7. A staple cartridge, comprising:

a cartridge body, comprising:

a proximal end;

a distal end;

a longitudinal axis extending between said proximal end and said distal end;

a deck configured to support patient tissue;

a first longitudinal row of staple cavities defined in said deck; and a second longitudinal row of staple cavities defined in said deck;

a plurality of first staples removably stored in said first longitudinal row of first staple cavities;

a plurality of second staples removably stored in said second longitudinal row of second staple cavities;

a longitudinal row of staple drivers, comprising:

a first staple driver translatable within a first staple cavity and a second staple cavity, wherein said first staple cavity is in said first longitudinal row of staple cavities and said second staple cavity is in said second longitudinal row of staple cavities; and a second staple driver translatable within a third staple cavity and a fourth staple cavity, wherein said third staple cavity is in said first longitudinal row of staple cavities and said fourth staple cavity is in said second longitudinal row of staple cavities, and wherein said first staple driver is positioned proximally with respect to said second staple driver; and a sled configured to lift said first staple driver from an unlifted position to a lifted position during a staple firing stroke, wherein said first staple driver is in contact with said cartridge body and said second staple driver when said first staple driver is in said lifted position.

8. The staple cartridge of claim 7, wherein said first staple driver comprises a first drive pillar that is configured to translate within said first staple cavity and a second drive pillar that is configured to translate within said second staple cavity during said staple firing stroke, wherein said first drive pillar comprises a first seat configured to drive a staple of said plurality of first staples and said second drive pillar comprises a second seat configured to drive a staple of said plurality of second staples during said staple firing stroke, wherein said first drive pillar is engaged with said cartridge body when said first staple driver is in said lifted position, and wherein said second drive pillar is engaged with said second staple driver when said first staple driver is in said lifted position.

9. The staple cartridge of claim 8, wherein said first drive pillar is engaged with said cartridge body and said second drive pillar is engaged with said second staple driver when said first staple driver is in said unlifted position.

10. The staple cartridge of claim 8, wherein said second drive pillar is not engaged with said second staple driver when said first staple driver is in said unlifted position.

11. The staple cartridge of claim 8, wherein said cartridge body further comprises a third longitudinal row of staple cavities defined in said deck, wherein said staple cartridge further comprises a plurality of third staples removably stored in said third longitudinal row of staple cavities, wherein said first staple driver further comprises a third drive pillar that is configured to translate within a fifth staple cavity during said staple firing stroke, wherein said fifth staple cavity is in said third longitudinal row of staple cavities, wherein said third drive pillar comprises a third seat configured to drive a staple of said plurality of third staples during said staple firing stroke, and wherein said third drive pillar is engaged with said cartridge body when said first staple driver is in said lifted position.

12. The staple cartridge of claim 11, wherein said second drive pillar is positioned intermediate said first drive pillar and said third drive pillar.

13. The staple cartridge of claim 8, wherein said cartridge body further comprises a third longitudinal row of staple cavities defined in said deck, wherein said staple cartridge further comprises a plurality of third staples removably stored in said third longitudinal row of staple cavities, wherein said first staple driver further comprises a third drive pillar that is configured to translate within a fifth staple cavity during said staple firing stroke, wherein said fifth staple cavity is in said third longitudinal row of staple cavities, wherein said third drive pillar comprises a third seat configured to drive a staple of said plurality of third staples during said staple firing stroke, and wherein said third drive pillar is engaged with said second staple driver when said first staple driver is in said lifted position.

14. The staple cartridge of claim 13, wherein said second drive pillar is positioned intermediate said first drive pillar and said third drive pillar.

* * * * *